US008907026B2

(12) United States Patent
Joffre et al.

(10) Patent No.: US 8,907,026 B2
(45) Date of Patent: *Dec. 9, 2014

(54) CROSSLINKABLE SACCHARIDE-SILOXANE COMPOSITIONS, AND NETWORKS, COATINGS AND ARTICLES FORMED THEREFROM

(75) Inventors: Eric Jude Joffre, Midland, MI (US); Joseph C. McAuliffe, Sunnyvale, CA (US); Csilla Kollar, Midland, MA (US); Xavier Thomas, Famars (FR); David C Gantner, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 1806 days.

This patent is subject to a terminal disclaimer.

(21) Appl. No.: 11/793,067

(22) PCT Filed: Dec. 22, 2005

(86) PCT No.: PCT/US2005/046780
§ 371 (c)(1),
(2), (4) Date: Jun. 15, 2007

(87) PCT Pub. No.: WO2006/071772
PCT Pub. Date: Jul. 6, 2006

(65) Prior Publication Data
US 2008/0138386 A1    Jun. 12, 2008

Related U.S. Application Data

(60) Provisional application No. 60/638,871, filed on Dec. 23, 2004.

(51) Int. Cl.
| C08G 77/38 | (2006.01) |
| C08L 83/04 | (2006.01) |
| D06M 23/00 | (2006.01) |
| D06M 15/643 | (2006.01) |
| A01N 25/34 | (2006.01) |
| A61K 8/893 | (2006.01) |
| C09D 183/06 | (2006.01) |
| C08G 77/42 | (2006.01) |
| D06M 15/03 | (2006.01) |
| A61Q 19/00 | (2006.01) |
| C08L 83/06 | (2006.01) |
| A61Q 5/00 | (2006.01) |
| A61Q 19/08 | (2006.01) |
| A61Q 15/00 | (2006.01) |

(52) U.S. Cl.
CPC . *A61K 8/893* (2013.01); *A61Q 5/00* (2013.01); *C09D 183/06* (2013.01); *C08G 77/42* (2013.01); *D06M 15/03* (2013.01); *A61Q 19/00* (2013.01); *A61Q 19/08* (2013.01); *A61Q 15/00* (2013.01); *D06M 15/643* (2013.01); *C08L 83/06* (2013.01)
USPC ......... 525/474; 524/588; 252/8.91; 252/8.61; 424/402

(58) Field of Classification Search
None
See application file for complete search history.

(56) References Cited

U.S. PATENT DOCUMENTS

| 2,676,182 | A | 4/1954 | Daudt et al. |
| 2,857,356 | A | 10/1958 | Goodwin |
| 3,159,601 | A | 12/1964 | Ashby |
| 3,220,972 | A | 11/1965 | Lamoreaux |
| 3,296,291 | A | 1/1967 | Chalk |
| 3,389,160 | A | 6/1968 | Reid |
| 3,419,593 | A | 12/1968 | Willing |
| 3,445,420 | A | 5/1969 | Kookootsedes et al. |
| 3,516,946 | A | 6/1970 | Modic et al. |
| 3,814,730 | A | 6/1974 | Karstedt |
| 3,936,582 | A | 2/1976 | Keiser |
| 3,989,667 | A | 11/1976 | Lee et al. |
| 3,989,668 | A | 11/1976 | Lee et al. |
| 4,263,274 | A | 4/1981 | Kulkarni |
| 4,269,603 | A | 5/1981 | Worth |
| 4,310,469 | A | 1/1982 | Crivello |
| 4,313,988 | A | 2/1982 | Koshar et al. |
| 4,370,358 | A | 1/1983 | Hayes et al. |
| 4,501,861 | A | 2/1985 | Woodbrey |
| 4,558,110 | A | 12/1985 | Lee |
| 4,584,355 | A | 4/1986 | Blizzard |
| 4,584,361 | A | 4/1986 | Janik |
| 4,585,836 | A | 4/1986 | Homan |
| 4,591,622 | A | 5/1986 | Blizzard |
| 4,591,652 | A | 5/1986 | DePasquale et al. |
| 4,604,442 | A | 8/1986 | Rich |

(Continued)

FOREIGN PATENT DOCUMENTS

| CA | 711756 | 6/1965 |
| CN | 1357022 | 7/2002 |

(Continued)

OTHER PUBLICATIONS

Akimoto, T. et al. Macromol. Chem. Phys. 2000, 201, 2729-2734.

(Continued)

*Primary Examiner* — Michael G Wityshyn
*Assistant Examiner* — Srikanth Patury
(74) *Attorney, Agent, or Firm* — Nixon Peabody LLP

(57) ABSTRACT

The invention provides a cross-linkable composition comprising a saccharide-siloxane copolymer according to a specified structural formula, a crosslinking agent, and, optionally, solvent. Cross-linked polymeric networks, cured coatings, and articles of manufacture formed from the inventive compositions are also provided, as well as processes and methods of manufacturing the inventive cross-linkable compositions and applications thereof.

22 Claims, 2 Drawing Sheets

(56) References Cited

U.S. PATENT DOCUMENTS

| | | | |
|---|---|---|---|
| 4,631,329 A | 12/1986 | Gornowicz |
| 4,707,531 A | 11/1987 | Shirahata |
| 4,760,025 A | 7/1988 | Estell et al. |
| 4,766,176 A | 8/1988 | Lee |
| 4,774,281 A | 9/1988 | Chaffee et al. |
| 4,784,879 A | 11/1988 | Lee et al. |
| 4,793,555 A | 12/1988 | Lee et al. |
| RE33,141 E | 1/1990 | Gornowicz et al. |
| 4,939,128 A | 7/1990 | Kato et al. |
| 4,962,076 A | 10/1990 | Chu et al. |
| 4,973,680 A | 11/1990 | Billmers |
| 4,999,437 A | 3/1991 | Dobler et al. |
| 5,004,791 A | 4/1991 | Billmers |
| 5,011,870 A | 4/1991 | Peterson |
| 5,015,700 A | 5/1991 | Herzig et al. |
| 5,017,654 A | 5/1991 | Togashi et al. |
| 5,036,117 A | 7/1991 | Chung et al. |
| 5,051,455 A | 9/1991 | Chu et al. |
| 5,053,442 A | 10/1991 | Chu et al. |
| 5,059,686 A | 10/1991 | Sau |
| 5,075,038 A | 12/1991 | Cole et al. |
| 5,082,914 A | 1/1992 | Cook et al. |
| 5,175,325 A | 12/1992 | Brown et al. |
| 5,227,093 A | 7/1993 | Cole et al. |
| 5,252,233 A | 10/1993 | Czech |
| RE34,606 E | 5/1994 | Estell et al. |
| 5,310,843 A | 5/1994 | Morita |
| 5,352,724 A | 10/1994 | Fujiki et al. |
| 5,380,527 A | 1/1995 | Legrow et al. |
| 5,428,142 A | 6/1995 | O'Lenick, Jr. |
| 5,493,041 A | 2/1996 | Biggs et al. |
| 5,498,703 A | 3/1996 | O'Lenick, Jr. |
| 5,583,244 A | 12/1996 | Uchida et al. |
| 5,654,362 A | 8/1997 | Schulz, Jr. et al. |
| 5,665,155 A | 9/1997 | Hohner et al. |
| 5,677,163 A | 10/1997 | Mainzer et al. |
| 5,700,676 A | 12/1997 | Bott et al. |
| 5,750,123 A | 5/1998 | Znaiden et al. |
| 5,831,080 A * | 11/1998 | Sejpka et al. ................ 536/124 |
| 5,891,977 A | 4/1999 | Dietz et al. |
| 5,895,794 A * | 4/1999 | Berg et al. .................... 523/217 |
| 5,972,682 A | 10/1999 | Bott et al. |
| 5,981,680 A | 11/1999 | Petroff et al. |
| 5,990,069 A | 11/1999 | Andre et al. |
| 6,051,216 A | 4/2000 | Barr et al. |
| 6,066,727 A | 5/2000 | Yamamoto et al. |
| 6,132,822 A | 10/2000 | Overcash et al. |
| 6,136,758 A | 10/2000 | Yamada et al. |
| 6,146,664 A | 11/2000 | Siddiqui |
| 6,218,560 B1 | 4/2001 | Abele et al. |
| 6,221,979 B1 | 4/2001 | Lin et al. |
| 6,239,194 B1 | 5/2001 | Standke et al. |
| 6,255,429 B1 | 7/2001 | Griffin et al. |
| 6,307,000 B1 | 10/2001 | Wong |
| 6,361,716 B1 | 3/2002 | Kleyer et al. |
| 6,372,833 B1 | 4/2002 | Chen et al. |
| 6,398,911 B1 * | 6/2002 | Schroeder et al. ......... 162/164.4 |
| 6,414,139 B1 | 7/2002 | Unger et al. |
| 6,433,055 B1 | 8/2002 | Kleyer et al. |
| 6,448,329 B1 | 9/2002 | Hirschi et al. |
| 6,465,550 B1 | 10/2002 | Kleyer et al. |
| 6,471,952 B1 | 10/2002 | Dubief et al. |
| 6,471,985 B2 | 10/2002 | Guyuron et al. |
| 6,482,969 B1 | 11/2002 | Helmrick et al. |
| 6,500,883 B1 | 12/2002 | Mack et al. |
| 6,517,933 B1 | 2/2003 | Soane et al. |
| 6,534,581 B1 | 3/2003 | Kleyer et al. |
| 6,762,289 B1 | 7/2004 | O'Lenick, Jr. et al. |
| 6,783,692 B2 | 8/2004 | Bhagwagar |
| 6,791,839 B2 | 9/2004 | Bhagwagar |
| 6,815,486 B2 | 11/2004 | Bhagwagar et al. |
| 7,005,281 B2 * | 2/2006 | Ohrlein et al. .................. 435/135 |
| 7,074,490 B2 | 7/2006 | Feng et al. |
| 7,199,205 B2 | 4/2007 | Okawa et al. |
| 7,205,373 B2 * | 4/2007 | Brandstadt et al. ............. 528/26 |
| 7,208,561 B2 | 4/2007 | Yoshitake et al. |
| 7,354,982 B2 | 4/2008 | Yoshitake et al. |
| 7,649,087 B2 | 1/2010 | Yoshitake et al. |
| 7,741,253 B2 * | 6/2010 | Hanes, Jr. ..................... 507/261 |
| 7,834,087 B2 | 11/2010 | Joffre et al. |
| 7,871,987 B2 | 1/2011 | McSuliffe et al. |
| 2001/0021387 A1 | 9/2001 | Krammer et al. |
| 2001/0053897 A1 * | 12/2001 | Frate et al. .................... 604/304 |
| 2003/0202948 A1 | 10/2003 | Koini et al. |
| 2004/0071746 A1 | 4/2004 | Popplewell et al. |
| 2004/0077816 A1 | 4/2004 | Brandstadt et al. |
| 2004/0082024 A1 | 4/2004 | Brandstadt et al. |
| 2004/0091541 A1 | 5/2004 | Unger |
| 2004/0091730 A1 | 5/2004 | Hart et al. |
| 2004/0241130 A1 | 12/2004 | Tamareselvy et al. |
| 2004/0247552 A1 | 12/2004 | Blin et al. |
| 2004/0254275 A1 | 12/2004 | Fukui et al. |
| 2005/0043365 A1 | 2/2005 | Yoshitake et al. |
| 2006/0013791 A1 | 1/2006 | Shimizu et al. |
| 2006/0216259 A1 | 9/2006 | Haubennestel |
| 2008/0199417 A1 | 8/2008 | Joffre et al. |
| 2008/0200612 A1 | 8/2008 | Joffre et al. |
| 2008/0209645 A1 | 9/2008 | Carrillo et al. |
| 2009/0258058 A1 | 10/2009 | Thomas et al. |
| 2010/0105582 A1 | 4/2010 | Joffre et al. |

FOREIGN PATENT DOCUMENTS

| | | |
|---|---|---|
| DE | 19918627 | 10/2000 |
| EP | 0180377 | 5/1986 |
| EP | 0363252 | 4/1990 |
| EP | 0438496 | 7/1991 |
| EP | 0444921 | 9/1991 |
| EP | 0465744 | 1/1992 |
| EP | 0506241 | 9/1992 |
| EP | 0572416 | 9/1992 |
| EP | 0347895 | 11/1993 |
| EP | 0698633 | 2/1996 |
| EP | 0562922 | 5/1997 |
| EP | 0848029 | 6/1998 |
| EP | 0865787 | 9/1998 |
| EP | 0869142 | 10/1998 |
| EP | 0874017 | 10/1998 |
| EP | 0934959 | 8/1999 |
| EP | 0962482 | 12/1999 |
| EP | 1020494 | 2/2000 |
| EP | 1057872 | 12/2000 |
| EP | 1331248 | 7/2007 |
| GB | 671721 | 5/1952 |
| GB | 2407496 | 5/2005 |
| JP | 62-68820 | 4/1987 |
| JP | 63 139106 | 6/1988 |
| JP | 05-112437 | 5/1993 |
| JP | 5-186596 | 7/1993 |
| JP | 5-331291 | 12/1993 |
| JP | 7-070204 | 3/1995 |
| JP | 8-134103 | 5/1996 |
| JP | 9-136901 | 5/1997 |
| JP | 10-298288 | 11/1998 |
| JP | 11-92490 | 4/1999 |
| JP | 11-343347 | 12/1999 |
| JP | 11-349601 | 12/1999 |
| JP | 2002-146025 | 5/2002 |
| WO | WO 90-03809 | 4/1990 |
| WO | WO 92-14428 | 9/1992 |
| WO | WO 94-29322 | 12/1994 |
| WO | WO 94-29324 | 12/1994 |
| WO | WO 96-18729 | 6/1996 |
| WO | WO 99-21892 | 5/1999 |
| WO | WO 00/02535 | 1/2000 |
| WO | WO 00-78844 | 12/2000 |
| WO | WO 01/30784 | 5/2001 |
| WO | WO 0134091 A2 * | 5/2001 |
| WO | WO 01-96450 | 12/2001 |
| WO | WO 02-088456 | 11/2002 |
| WO | WO 03-020770 | 3/2003 |
| WO | WO 03-042283 | 5/2003 |
| WO | WO 03-050144 | 6/2003 |
| WO | WO 2004-016626 | 2/2004 |

(56) References Cited

FOREIGN PATENT DOCUMENTS

| | | |
|---|---|---|
| WO | WO 2004/024799 | 3/2004 |
| WO | WO 2004-108175 | 12/2004 |
| WO | WO 2005-047378 | 5/2005 |
| WO | WO 2005-063855 | 7/2005 |
| WO | WO 2006-025552 | 3/2006 |
| WO | WO 2006-064928 | 6/2006 |
| WO | WO 2006-065282 | 6/2006 |
| WO | WO 2006-066227 | 6/2006 |
| WO | WO 2006-107003 | 10/2006 |
| WO | WO 2006-107004 | 10/2006 |
| WO | WO 2006-127882 | 11/2006 |
| WO | WO 2006-127883 | 11/2006 |
| WO | WO 2007-139812 | 12/2007 |
| WO | WO 2008-046763 | 4/2008 |
| WO | WO 2008-103219 | 8/2008 |
| WO | WO 2009-125126 | 10/2009 |

OTHER PUBLICATIONS

Database WPI Derwent Publications Ltd., London, GB; AN 1988-201757 (XP002395828).

Gupta et al. Biotechnol. Appl. Biochem. (2003) 37: 63-71.

Wrodnigg, T., Eder, B. *The Amadori and Heyns Rearrangements: Landmarks in the History of Carbohydrate Chemistry or Unrecognized Synthetic Opportunities* Topic in Current Chemistry vol. 215 2001 dg. 115-152.

Written Opinion of the International Searching Authority corresponding to International Patent Application No. PCT/US2005/046780, European Patent Office, dated Sep. 8, 2006, 5 pages.

International Search Report corresponding to International Patent Application No. PCT/US2005/046780, European Patent Office, dated Sep. 8, 2006, 2 pages.

Wagner et al., *Silicon-Modified Carbohydrate Surfactants III: Cationic and Anionic Compounds*, Applied Organometallic Chemistry, vol. 11, 523-538 (1997).

* cited by examiner

CROSSLINKABLE SACCHARIDE-SILOXANE COMPOSITIONS, AND NETWORKS, COATINGS AND ARTICLES FORMED THEREFROM

CROSS-REFERENCE TO RELATED APPLICATION

This application is a nationalization of PCT/US2005/046780 filed on Dec. 22, 2005, which claims benefit to U.S. Provisional Application No. 60/638,871, filed on Dec. 23, 2004.

BACKGROUND OF THE INVENTION

This invention relates to crosslinkable compositions comprising saccharide-siloxane copolymers and a crosslinking agent. The copolymers comprise a saccharide-derived polyhydroxyl-functional moiety covalently linked to an organosilicon backbone. The crosslinkable copolymers form a crosslinked network in the presence of reactive crosslinking agents which link the copolymers via the polyhydroxy-functionality of the saccharide components. The invention further relates to the crosslinked networks, cured coatings, and articles of manufacture comprised thereof.

Organosiloxanes comprising a saccharide component, and process for making them are known in the art. Saccharides comprising aldonolactones are particularly suitable for linking to amine-functional organosilicons. For example, U.S. Pat. No. 4,591,652 describes manufacturing polyhydroxyl silanes by reacting silanes having amine-terminated substituents with aldonic acid lactones. Japanese patent No. 62-68820 discloses organopolysiloxanes comprising saccharide residues made from aminosiloxanes and saccharide lactones. WO 94/29324 describes siloxanyl-modified compounds, methods for their preparation and applications as surface-active and surface-modifying agents, particularly in plant protection. It more particularly discloses surface-active or surface-modifying agents formed from epoxy-trisiloxane reaction products and saccharide lactones. WO 02/088456 describes amido-functional aminopolydiorganosiloxanes, a method for the production thereof, preparations comprising the amido-functional aminopolydiorganosiloxanes and applications in the textile industry. The amido-functional siloxanes are formed from reacting aminosiloxanes and saccharide lactones.

Other processes for covalently linking saccharide molecules and silicone-based compounds, including polydialkylsiloxanes, are also known. For example, U.S. Pat. No. 5,831,080 describes organosilicon compounds comprising glycoside radicals made by hydrosilylating allyl functional saccharide groups. U.S. Pat. No. 6,517,933 B1 describes a hybrid polymer material comprising a set of naturally occurring building blocks, which include saccharides, and a set of synthetic building blocks that include polysiloxanes. A number of potential linking chemistries are described. U.S. Patent Application Serial No. 20040082024 to Brandstadt et al. discloses ester linked saccharide-siloxanes and enzyme-catalyzed esterification processes. All of this referenced art describes saccharide-siloxane copolymers comprising polyhydroxy functionality that may be suitably employed in the present invention. The prior-cited art is fully incorporated herein by reference.

There is some technology directed to crosslinking of saccharides, and other polyhydroxylpolymers and to the materials comprised thereof. For instance, U.S. Pat. No. 6,132,822 discloses a high gloss coated sheet material made from a porous sheet and coating comprising a water dispersible crosslinkable polymer and a water dispersible film-forming polymer. '822 teaches polyhydroxyl polymers like poly(vinyl alcohol) as preferred crosslinkable polymers. The preferred crosslinking agents disclosed are glyoxal, epichlorohydrin, metal ions, fatty acid complexes of metal ions, and exposure to energy.

U.S. Pat. No. 5,252,233 describes a heat curable hydrophilic finish produced on cellulose-containing textiles used to impart durability to hydrophilic textiles. The finishing agent comprises: 1) an organo-modified silicone containing either hydroxy-terminal polyether groups or hydroxyl groups derived from 3,4-epoxycyclohexyl ethyl or 3-glycidyloxypropyl groups; 2) glyoxal; 3) glycol; and 4) a acidic catalyst.

U.S. Pat. No. 4,269,603 describes a process for imparting durable press properties to a textile fabric formed at least partly of cellulosic fibers using a finishing agent. The finishing agent comprises glyoxal, reactive silicone and a catalyst.

DE Patent No. 19918627 describes a novel polymer composition comprising water-soluble polymers, silicon oxide components, and titanate or zirconate crosslinkers. The water-soluble polymers are polysaccharides, proteins or cellulose derivatives. The silicone compounds are alkoxysilane hydrolysates. The hybrid polymers are proposed as carrier systems for the controlled release of drugs.

U.S. Patent Application Serial No. 2004 0091730 A1 describes a wood product made from sequentially treating wood with two solutions. The penetrating solution contains boric acid, a metallocene catalyst, a free radical initiator, a film forming polymer and adhesion promoter. The topcoat includes a film-forming polymer. The film-forming polymer is an acrylic or siloxane based polymer or copolymer. The metallocene catalyst contains tin or titanate.

Organosiloxane-based elastomers formed from crosslinking organosiloxane polymers are well known in the art and such materials have wide-ranging utility as coatings which confer desirable surface properties to the coated substrate, for example, enhanced resistance to wear, thermal stability, hydrophobicity and resistance to water, adhesion control and release, frictional control including anti-slip capability, and so on. Various fillers and other additives may be included within the elastomeric matrix to provide coatings with even more varied performance benefits. The mechanical, chemical and ionic characteristics of the crosslinked network matrix influences both the nature and amount of additives that may suitably be included. Compositions and cured coating compositions comprising crosslinked carbohydrates are known in the art. However, the present inventors are unaware of compositions and cured coating compositions comprising saccharide-siloxane copolymers crosslinked via the polyhydroxyl functionality of the saccharide. The networked matrix and cured coatings formed from these unique crosslinkable compositions would provide a blended property profile comprising attributes of both silicone and carbohydrate-based matrices which may support, retain and/or controllably release a variety of additives. Crosslinking via the saccharide component of the copolymer yields elastomers possessing a property profile making them desirable for particular applications.

Hence, there is a need in the art for crosslinkable compositions comprising saccharide-siloxane copolymers wherein the saccharide-siloxanes form a crosslinked network by linking between the hydroxyl functionalities possessed by the polyhydroxyl saccharide-derived backbone of the copolymers. There is also a need in the art for cured coating compositions comprised therefrom, which reflect the benefits and characteristics known to be imparted by coatings that comprise both silicone and carbohydrate components, as well as the unique properties which may be conferred by a cured matrix comprising a saccharide to saccharide linked network. There is a further need in the art for coatings that confer improved such benefits and characteristics to the coated substrate, and the improved substrates and articles comprising them.

SUMMARY OF THE INVENTION

Accordingly, the present invention is based on the surprising discovery that saccharide-derived polyhydroxyl siloxanes form crosslinked networks via linking between the saccharides in the presence of a suitably reactive crosslinking agent, for example, borate or titanate esters and acids. The present invention provides novel, crosslinkable compositions comprising saccharide-siloxane copolymers wherein the crosslinking substantially occurs between the hydroxy-functional groups of the saccharide components, and cured coating compositions comprising the crosslinked networks. Synthetic processes thereof are also provided. The crosslinking occurring between the hydroxyl functionalities of the saccharide backbone of the copolymers is unique and forms a three-dimensional network having a unique matrix. Consequently, the films and coatings formed therefrom possess unique property profiles. While not being bound by theory, the resulting films combine the properties of siloxanes like, softness, vapor permeability, hydrophobicity, good aesthetic feel, adhesive release, & flexibility with the attributes of saccharides like substantivity to substrates containing hydroxyl groups or polar groups, e.g. wood, cellulose, cotton or skin. The unique hydrophilic & hydrophobic nature of these materials allows compatibility with a wide range of molecules, including biomaterial such as enzymes.

These crosslinked films may be used as adhesive release coatings on paper, as wood water repellents, or as wound dressings. These films may also provide film-forming attributes for personal care products for hair, skin or antiperspirants. The crosslinkable composition in solvents may provide gellant properties desirable for other applications. Articles of manufacture comprising the novel cured coating compositions may be adapted for a variety of useful functions, including but not limited to providing preservative, protective, defensive, and/or reactive functions to textiles and clothing, including those intended to be worn in the context of provision or receipt of health care services or during military engagement.

One embodiment provides a crosslinkable composition. The crosslinkable composition comprises: a) a saccharide-siloxane copolymer; b) a crosslinking agent; and c) optionally, a solvent. The saccharide-siloxane copolymer has the following formula:

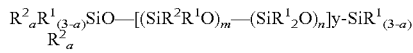

wherein $R^1$ can be the same or different and comprises hydrogen, $C_1$-$C_{12}$ alkyl, an organic radical, or $R^3$-Q, Q comprises an epoxy, cycloepoxy, primary or secondary amino, ethylenediamine, carboxy, halogen, vinyl, allyl, anhydride, or mercapto functionality, m and n are integers between 0 and 10,000 and may be the same or different, a is independently 0, 1, 2, or 3, y is an integer such that the copolymer has a molecular weight less than 1 million, $R^1_{(3-a)}SiO$—$[(SiR^1O)_m$—$(SiR^1_2O)_n]_y$—$SiR^1_{(3-a)}$ comprises an organosiloxane polymer component, $R^2$ has the formula Z-$(G^1)_b$-$(G^2)_c$, and there is at least one $R^2$, wherein $G^1$ is a saccharide component comprising 5 to 12 carbons, b+c is 1-10, b or c can be 0, either b or c must be 1, and a is 0-3, $G^2$ is a saccharide component comprising 5 to 12 carbons additionally substituted with organic or organosilicon radicals, Z is a linking group between the organosiloxane polymer component and the saccharide component and is independently selected from the group consisting of:

—$R^3$—NHC(O)—$R^4$—;
—$R^3$—NHC(O)O—$R^4$—;
—$R^3$—NH—C(O)—NH—$R^4$—;
—$R^3$—C(O)—O—$R^4$—;
—$R^3$—O—$R^4$—;
—$R^3$—CH(OH)—$CH_2$—O—$R^4$—;
—$R^3$—CH(OH)—$CH_2$—NH—$R^4$—; and
—$R^3$—N($R^1$)—$R^4$, and $R^3$ and $R^4$ are spacer groups comprising $R^5R^6R^7$, and $R^5$ and $R^7$ are either $C_1$-$C_{12}$ alkyl or $((C_1$-$C_{12})O)_p$ where p is any integer 1-50 and each $(C_1$-$C_{12})O$ may be the same or different, $R^6$ is —N($R^8$)—, where $R^8$ is H or $C_1$-$C_{12}$ alkyl, and at least one of $R^3$ and $R^4$ must be present and may be the same or different, at least one of $R^5$, $R^6$ and $R^7$ must be present and may be the same or different, and wherein the saccharide-siloxane copolymer comprises a reaction product of a functionalized organosiloxane polymer and at least one polyhydroxy-functional saccharide such that the organosiloxane is covalently linked via the linking group, Z, to the at least one polyhydroxy-functional saccharide.

The crosslinking agent comprises any agent capable of crosslinking a hydroxyl-functional polymer.

In further embodiments, the crosslinkable composition may comprise one or more other additives as desired for specific applications. A non-limiting list of possible additives include: d) a catalyst; e) a filler; f) a pigment; g) a UV stabilizer; h) a thermal stabilizer; i) a rheology modifier; j) a thickener; k) an adhesion promoter; l) a biocide; m) a preservative; n) an enzyme; o) a peptide; p) a pressure sensitive adhesive or q) a surface active agent.

Methods for making the crosslinkable compositions are also provided. In one such embodiment the method comprises the steps of: a) dissolving a saccharide-siloxane copolymer in a suitable solvent to form a solution; b) dissolving at least one crosslinking agent in a suitable solvent to form a solution; c) adding the solution from b) into the solution from a) and mixing until b) is dispersed in a). The saccharide-siloxane copolymer comprises a reaction product of a functionalized organosiloxane polymer and at least one polyhydroxy-functional saccharide such that the organosiloxane polymer is covalently linked via a linking group to at least one polyhydroxyl-functional saccharide. In additional embodiments, other ingredients may be added. The additives are optional and may be included at none, one, some or all of steps a), b) and c), and are mixed until dispersed. Some may require pre-dissolution in a suitable vehicle such as a solvent. The degree to which the additive incorporates into the matrix, and the ionic character of the additive influence the timeframe of addition. Such additives may include but are not limited to: d) a catalyst; e) a filler; f) a pigment; g) a UV stabilizer; h) a thermal stabilizer; i) a rheology modifier; j) a thickener; k) an adhesion promoter; l) a biocide; m) a preservative; n) an enzyme; o) a peptide; p) a pressure sensitive adhesive, or any surface active agent.

Other embodiments provide crosslinked networks and cured coatings formed from the crosslinkable compositions. Coating embodiments include adhesive release coatings on paper, wood water repellents and sealants, and, wound dressings or liquid bandages. Another embodiment provides articles of manufacture comprising the inventive cured coatings. Such articles include textiles and, specifically, clothing, wherein the cured coating composition comprises additives that confer a protective, biocidal, preservative or bio-defensive quality to the articles.

DETAILED DESCRIPTION OF THE INVENTION

Figure 1A:
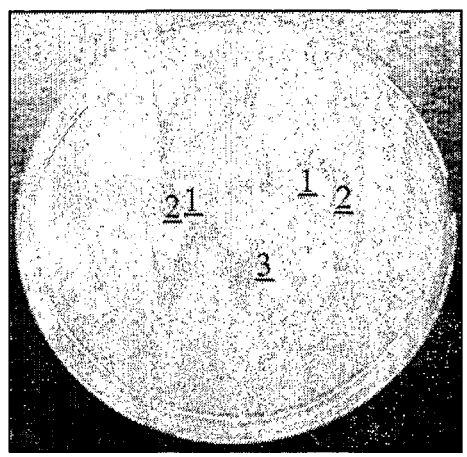
FIG. 1: illustrates the release of Protease B enzyme from a prepared saccharide siloxane copolymer formulation patch on a skim milk plate 24 hours incubation.

The present invention is based on the surprising discovery that a class of copolymers comprised of the reaction product of a functionalized organosiloxane polymer and at least one polyhydroxy-functional saccharide wherein the organosiloxane is covalently linked via a linking group to the at least one polyhydroxy-functional saccharide, crosslinks to form a three-dimensional network in the presence of a reactive crosslinker. Crosslinkable compositions comprise one or more saccharide-siloxane copolymers and one or more suitable crosslinking agents. The compositions may optionally comprise other ingredients including, for example, suitable solvents, fillers, pigments, rheology modifiers, surface-active agents, adhesion promoters, catalysts, and even bioactive compounds such as enzymes. Due to the unique characteristics, for example hydrophobicity and hydrogen bonding, of the network matrix formed from the crosslinkable compositions, the three-dimensional network matrix may incorporate, suspend, retain and release additives and combinations of additives which yield cured coating compositions particularly suitable for specific applications.

One embodiment provides a crosslinkable composition comprising: a) a saccharide-siloxane copolymer; b) a crosslinking agent; and c) optionally, a solvent. In this embodiment, the crosslinking is self-catalyzing. The saccharide-siloxane copolymer has the following formula:

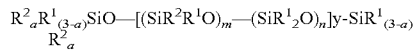

wherein $R^1$ can be the same or different and comprises hydrogen, $C_1$-$C_{12}$ alkyl, an organic radical, or $R^3$-Q, Q comprises an epoxy, cycloepoxy, primary or secondary amino, ethylenediamine, carboxy, halogen, vinyl, allyl, anhydride, or mercapto functionality, m and n are integers between 0 and 10,000 and may be the same or different, a is independently 0, 1, 2, or 3, y is an integer such that the copolymer has a molecular weight less than 1 million, $R^1_{(3-a)}SiO$—$[(SiR^1O)_m$—$(SiR^1_2O)_n]_y$—$SiR^1_{(3-a)}$ comprises an organosiloxane polymer component, $R^2$ has the formula $Z$-$(G^1)_b$-$(G^2)_c$, and there is at least one $R^2$, wherein $G^1$ is a saccharide component comprising 5 to 12 carbons, b+c is 1-10, b or c can be 0, either b or c must be 1, $G^2$ is a saccharide component comprising 5 to 12 carbons additionally substituted with organic or organosilicon radicals, Z is a linking group between the organosiloxane polymer component and the saccharide component and is independently selected from the group consisting of:

—$R^3$—NHC(O)—$R^4$—;
—$R^3$—NHC(O)O—$R^4$—;
—$R^3$—NH—C(O)—NH—$R^4$—;
—$R^3$—C(O)—O—$R^4$—;
—$R^3$—O—$R^4$—;
—$R^3$—CH(OH)—CH$_2$—O—$R^4$—;
—$R^3$—CH(OH)—CH$_2$—NH—$R^4$—; and
—$R^3$—N($R^1$)—$R^4$, and $R^3$ and $R^4$ are spacer groups comprising $R^5R^6R^7$, and $R^5$ and $R^7$ are either $C_1$-$C_{12}$ alkyl or $((C_1$-$C_{12})O)_p$, where p is any integer 1-50 and each $(C_1$-$C_{12})O$ may be the same or different, $R^6$ is —$N(R^8)$—, where $R^8$ is H or $C_1$-$C_{12}$ alkyl, and at least one of $R^3$ and $R^4$ must be present and may be the same or different, at least one of $R^5$, $R^6$ and $R^7$ must be present and may be the same or different, and wherein the saccharide-siloxane copolymer comprises a reaction product of a functionalized organosiloxane polymer and at least one polyhydroxy-functional saccharide such that the organosiloxane is covalently linked via the linking group, Z, to the at least one polyhydroxy-functional saccharide.

It will be apparent to one of ordinary skill in the art that in order to achieve the desired crosslinking rather than mere elongation of the polymer, either or both of the crosslinking agent and crosslinkable copolymers must have a functionality of three. In one specific embodiment the crosslinkable composition comprises a saccharide-siloxane copolymer comprising hydroxyl functionality of at least three.

The crosslinkable saccharide-siloxanes suitable for inclusion in the present crosslinkable compositions comprise the reaction product of an organosiloxane and a polyhydroxy-functional saccharide wherein the organosiloxane and saccharide are covalently linked via at least one linking group. In one embodiment the linking group comprises an amide, amino, urethane, urea, ester, ether, thioether, or acetal linking group.

The crosslinkable compositions yield films and coatings having a wide range of characteristics depending on several variables, including the specific crosslinkable copolymer selected to comprise the composition. It is contemplated that a crosslinkable composition may comprise a single species or a combination of different species in predetermined ratios. In one specific embodiment the crosslinkable copolymer is the reaction product of a functionalized organosiloxane and at least one polyhydroxy-functional saccharide comprising an aldonic acid or an oligoaldonic acid. In a more specific embodiment the aldonic acid or the olgoaldonic acid comprises a lactone. Aldonolactones are particularly suitable saccharides when the organosiloxane comprises amino-functionality. In very specific embodiments the crosslinkable composition comprises the reaction product of an amino-functional organosiloxane and a lactone.

Two exemplary lactones include gluconolactone (GL) and lactobionolactone (LBL). Both gluconolactone (GL) and lactobionolactone (LBL) are commercially available. Gluconic acid, found naturally occurring in cells, is a polyhydroxy alpha-hydroxy aldonic acid known to provide beneficial effects to skin and hair. It is currently contained in products marketed as personal care products in the gluconolactone form. Lactobionic acid (4-O-beta-D-galactopyranosyl-D-gluconic acid) is comprised of a galactose molecule attached to one molecule of gluconic acid via an ether-like linkage. Galactose is a chemically neutral, endogenous hexose sugar utilized in glycosaminoglycan synthesis, collagen synthesis, and wound-healing applications. Lactobionic acid is formed by oxidation of the disaccharide lactose (milk sugar) and has current application in the pharmaceutical industry in a salt form for intravenous delivery of erythromycin and in mineral supplementation. A major commercial application is in the organ transplant art as a constituent of organ preservation fluid. This function relates to its ability to suppress tissue damage caused by oxygen radicals and is thought to be mediated through inhibition of hydroxyl radical production via complexation of FeII. Recent work suggests efficacy in the personal care industry, particularly in products directed to skin care and anti-aging formulations. Hence, in very specific embodiments the crosslinkable composition comprises the reaction product of an amino-functional organosiloxane and either GL or LBL.

Crosslinkers suitable for the present crosslinkable compositions must be chemically reactive with hydroxyl groups and must be able to react with at least two hydroxyl groups. While not being bound by theory, the linking of the polyhydroxyl functionality on separate polymers develops the three dimensional network required to form a crosslinked film. The crosslink density is determined by both the mole ratio of crosslinker to polyhydroxyl functionality, and the separation distance of the polyhydroxyl functional sites along the saccharide-siloxane copolymer backbone. In one embodiment of the crosslinkable composition, the crosslinking agent is any agent capable of crosslinking a hydroxy-functional polymer. Saccharide-siloxanes typically need three or more primary hydroxyl groups in order to crosslink into three-dimensional networks. Alternatively, as in the case of siloxanes end-blocked with groups such as glucolactone, trifunctional crosslinkers are employed to yield the three-dimensional networks.

The crosslinker may be selected from the following non-limiting list: boric acid, borate ester (e.g. tri-n-propyl borate, triisopropanolamine borate), alkyl boronic acid or ester (e.g. phenyl boronic acid), titanate, (e.g. titanium isopropoxide, diisopropoxytitanium bis(acetylacetonate)), zirconate, glyoxal, gluteraldehyde, epichlorohydrin, urea-formaldehyde, zirconium ammonium carbonate, salt of a multivalent ion, bifunctional epoxy or glycidyl compounds (e.g. 1,4 butanediol diglycidyl ether), di-(N-hydroxymethyl)urea, di-isocyanate (e.g. toluene diisocyante, hexamethylene diisocyanate), 2-chloro N,N di-ethylacetamide, sodium trimetaphosphate, phosphorous oxychloride, acrolein, N-methyl urea, dicarboxylic acid, bis-acid chloride, dialkyldichlorosilane (e.g. dimethyldichlorosilane), alkyltrichlorosilane (e.g. Methyltrichlorosilane), reactive siloxane resin, and combinations thereof.

In one embodiment the crosslinking agent comprises a reactive siloxane resin. In a more specific embodiment, the reactive siloxane resin comprises a hydroxy-functional or vinyl-functional. In a very specific embodiment the reactive siloxane resin comprises a hydroxyl-functional resin in a weight ratio of about 28 pts resin to 100 pts saccharide-siloxane copolymer, and in an even more specific embodiment, the reactive siloxane resin comprises a hydroxy-functional resin in a weight ratio of about 25 pts resin to 100 pts saccharide-siloxane copolymer. In another specific embodiment the reactive siloxane resin comprises a vinyl-functional resin and a weight ratio of about 40 parts resin to 100 parts saccharide-siloxane copolymer.

The saccharide-siloxane copolymers and crosslinking agent can be delivered neat or from a carrier solvent or as an emulsion. The solvent of choice can be a polar or non-polar solvent or combination of solvents. Two useful combinations of carrier solvents are paraffin/alcohol and siloxanes/alcohol.

The crosslinkable composition may further comprise one or more additives. Non-limiting examples of suitable additives include: d) catalysts; e) fillers; f) pigments; g) UV stabilizers; h) thermal stabilizers; i) rheology modifiers; j) thickeners; k) adhesion promoters; l) biocides; m) preservatives; n) enzymes; o) peptides; p) pressure sensitive adhesives, q) surface-active agents, or any combination thereof.

In one embodiment the crosslinkable composition further comprises at least one additive comprising a catalyst. In one embodiment, the catalyst comprises a chemical catalyst capable of catalyzing crosslinking reactions. Non-limiting examples include metal-based catalysts for hydrosilylations and olefin metathesis based on Pt and Rh respectively. In another specific embodiment, the catalyst comprises a bio-catalyst, and more specifically, an enzyme. In one aspect, the crosslinking agent comprises dicarboxylic acid and the catalyst comprises an enzyme capable of catalyzing an esterification or transesterification reaction.

The use of enzymes as catalysts eliminates the need for self-catalyzing reactive linkers, which may be expensive and prone to decomposition and/or hydrolysis. In addition, the enzyme may attach the crosslinker with regio- and stereo-selectivity. For instance, the enzyme may promote crosslinking solely to the primary hydroxyl groups of the saccharide-siloxane. Such regio- and stereo-specific linking via enzymes is disclosed in detail in U.S. Patent Application Serial No. 20040082024, fully incorporated herein by reference. In cases where the enzyme is specific to primary hyroxyls, the saccharide-siloxane copolymer needs three or more primary hydroxyl groups in order to form a three-dimensional crosslinked network. Hence, in the case of certain polymers wherein the saccharide endblocks the siloxane, such as in gluconolactone-endblocked siloxanes, three-dimensional crosslinking will not occur unless an at least trifunctional crosslinker is used.

It will be apparent to one of ordinary skill in the art that crosslinkable, compositions providing such homogeneous spatial and/or ionic networks in the films and coatings formed therefrom offer suitability for a variety of particular applications, for example electronics, wherein such a property profile is desirable. In a specific embodiment, the enzyme comprises a lipolytic enzyme, and in a very specific embodiment, the lipolytic enzyme, or lipase, comprises N4435.

As used herein, the term "enzyme" includes proteins that are capable of catalyzing chemical changes in other substances. The enzymes can be wild-type enzymes or variant enzymes. Enzymes within the scope of the present invention include, but are not limited to, pullulanases, proteases, cellulases, amylases, isomerases, lipases, esterases, acyltransferases, oxidases, oxidoreductases, hydrolases, aldolases, ketolases, glycosidases, oxidoreductases, hydrolases, aldolases, ketolases, glycosidases, lyases, ligases, transferases, and ligases.

As used herein, the term "lipolytic enzyme" refers to a polypeptide, protein or enzyme exhibiting a lipid degrading capability such as a capability of degrading a triglyceride, ester or a phospholipid. A lipolytic enzyme may be, for example, a lipase, a phospholipase, an esterase or a cutinase. For the present invention, lipolytic activity may be determined according to any procedure known in the art. See, for example, Gupta et al, Biotechnol. Appl. Biochem. (2003) 37:63-71; Andre, Christophe, et al, U.S. Pat. No. 5,990,069 (International Publication WO 96/18729A1).

As used herein, the term "protein" refers to polymers of large molecular mass composed of one or more polypeptide chains and whose monomers are amino acids joined together by peptide bonds. The terms "protein" and "polypeptide" are sometimes used interchangeably herein.

The crosslinkable compositions may further comprise at least one additive comprising a filler. Fillers known in the art include those categorized as reinforcing and/or extending. Non-limiting exemplary reinforcing fillers include treated, fumed or untreated silica. Reinforcing fillers may lead to tighter network formation in the cured coatings derived from the crosslinkable compositions, making the coatings more suitable for particular applications. Examples of extending fillers can include precipitated or ground calcium carbonate, talc, mica; kaolin, clay, titanium dioxide, wollastonite, zeolites and diatomaceous earth. In one embodiment the crosslinkable composition comprises at least one additive comprising a filler wherein the filler comprises a fumed silicon dioxide.

The crosslinkable composition may further comprise at least one additive comprising a pigment. Because of the hybrid nature of the networked matrix formed from the crosslinkable compositions, either or both of organic and inorganic pigments may be incorporated. One of ordinary skill in the art will appreciate the wide variety of suitable pigments and that selection is dependent upon a given downstream coating application.

The crosslinkable compositions may further comprise at least one additive comprising a rheology modifier. Modification to the flow property of the coating may be achieved by the addition of, for example, thickeners or thixotropic agents. Thickeners suitable for emulsion embodiments include cellulosic, polyacrylic or urethane associative thickeners.

In addition, the crosslinkable compositions may further comprise at least one additive comprising an adhesion promoter. Adhesion promoters that are suitable to practice the present invention include those having at least one hydrolysable group and having the formula:

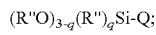

wherein R" is an alkyl or haloalkyl radical with up to 8 carbon atoms,

Q is a saturated, unsaturated or aromatic hydrocarbon radical functionalized by a group selected from amino, mercapto, ether, epoxy, isocyanato, cyano, isocyanurate acryloxy and acyloxy and mixtures thereof, and q is 0 to 3.

Examples of silanes that act as adhesion promoters include aminoorganotrialkoxysilanes, ethylpolysilicate, 1,3,5-tris (trimethoxysilylpropyl) isocyanurate and glycidoxyorganotrialkoxysilane. Typical aminoorganotrialkoxysilanes include gamma-aminopropyltriethoxysilane, N-beta-aminoethyl-gamma-aminopropyltrimethoxysilane, gamma-aminopropyltrimethoxysilane, (ethylenediaminepropyl)trimethoxysilane, and combinations thereof. Typical glycidoxyorganotrialkoxysilanes include gamma-(glycidoxy)propyltrimethoxysilane. The amount of silane adhesion promoters added to the inventive compositions is typically relatively small, usually less than about one weight percent of the composition, and in specific embodiments, less than about 0.5 weight percent.

The crosslinkable compositions may further comprise one or more additives comprising a pressure sensitive adhesive. The pressure sensitive adhesive may be selected from the following examples of known pressure sensitive adhesives: polyisoprene, polystyrene, polyethylene, polybutadiene, polyisobutylene, polyethylene/butylenes, styrene/butadiene, styrene-butadiene-styrene, styrene-isoprene-styrene, styrene-ethylene/butylene-styrene block copolymers butyl rubber, polytetrafluoroethylene, polyvinyl chloride, polyvinylidene chloride, polychloroprene, polyacrylonitrile, polychlorodiene, polysiloxane, and mixtures thereof.

The crosslinked network matrix formed from the inventive crosslinkable compositions provide a particularly suitable environment for organic and bio-additives. In one such embodiment the crosslinkable composition further comprises an additive wherein the additive comprises an enzyme. In these embodiments the enzyme may be incorporated into the crosslinkable composition such that it is contained within the crosslinked network matrix with varying degrees of desired retention. In one embodiment it is contemplated that the enzyme remains incorporated in the matrix and in other embodiments it is contemplated that the enzyme will slowly leach from the matrix.

In specific embodiments a cured coating forms from a crosslinkable composition comprising an enzyme wherein the cured coating is applied to a substrate such that the enzyme imparts a bioactive function to the substrate. This function may be proactive, defensive or protective in that it shields the substrate from undesirable agents and/or the effects thereof, and/or inhibits the growth of undesirable agent upon or within the substrate. The function may be offensive or reactive in that it acts upon undesirable agents present on the substrate. Non-limiting examples of enzymes suitable for this invention include those sold by Genencor International under the trade names Purafect, Purastar, Properase, Puradax, Clarase, Multifect, Maxacal, Maxapem, and Maxamyl (U.S. Pat. No. 4,760,025 and WO 91/06637); and those sold by Novo Industries A/S (Denmark) under the trade names Alcalase, Savinase, Primase, Durazyme, Duramyl, Lipolase, and Termamyl. In one specific embodiment the enzyme comprises a protease.

Proteases and other enzymes are typically produced by aerobic fermentation of bacteria or fungi. These enzymes are generally secreted as extracellular proteins, but in some cases, enzymes can be isolated from the cell membrane or from within the cell by chemical, enzymatic or physical disruption. Proteases are carbonyl hydrolases which generally act to cleave peptide bonds of proteins or peptides. As used herein, "protease" means a naturally-occurring protease or a recombinant protease. Naturally-occurring proteases include alpha-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

The protease can be of animal, plant, or microorganism origin. For example, the protease may be a serine proteolytic enzyme of bacterial origin. Purified or nonpurified forms of enzyme may be used. Protease enzymes produced by chemically or genetically modified mutants are included by definition, as are close structural enzyme variants. Particularly preferred by way of protease enzyme is bacterial serine proteolytic enzyme obtained from *Bacillus*, particularly subtilases, for example *Bacillus subtilis, Bacillus lentus, Bacillus amyloliquefaciens*, and/or *Bacillus licheniformis*. Suitable commercial proteolytic enzymes which may be considered for inclusion in the present invention compositions include Alcalase®, Esperase®, Durazym®, Everlase®, Kannase®, Relase®, Savinase®, Maxatase®, Maxacal®, and Maxapem® 15 (protein engineered Maxacal); Purafect®, Properase® (protein engineered Purafect) and subtilisin BPN and BPN'.

Protease enzymes also encompass protease variants having an amino acid sequence not found in nature, which is derived from a precursor protease by substituting a different amino acid sequence not found in nature, which is derived from a precursor protease by substituting a different amino acid for the amino acid residue at a position in said protease equivalent to positions equivalent to those selected from the group consisting of +76, +87, +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in U.S. Pat. No. RE 34,606; U.S. Pat. Nos. 5,700,676; 5,972,682 and/or 6,482,628, which are incorporated herein by reference in their entirety.

Exemplary protease variants include a subtilisin variant derived from *Bacillus lentus*, as described in U.S. Pat. No. RE 34,606; a Y217L variant derived from *Bacillus amyloliquefaciens*, as described in U.S. Pat. No. 5,700,676, hereinafter referred to as Protease B; a modified bacterial serine proteolytic enzyme described in U.S. Pat. No. 6,482,628; and a modified bacterial serine proteolytic enzyme described in U.S. Pat. No. 5,972,682. Also suitable is LG12 a *B. subtilis* as described in U.S. Pat. No. 5,677,163, which is incorporated by reference herein. Other proteases useful in the practice of this invention can be selected from the group consisting of Savinase®, Esperase®, Maxacal®, Purafect®, BPN' and mixtures thereof. In a very specific embodiment, the enzyme comprises Protease B. Among other functions, Protease B enables the digestion of necrotic tissue and has desirable applications in wound debridement.

An additional embodiment is directed to an article of manufacture comprising a cured coating formed from a crosslinkable composition comprising an enzyme and an adhesion release agent such that the article functions as a releasable bioactive coating, for example, a band-aid. In further specific embodiments articles such as textiles are provided which comprise cured coatings formed from crosslinkable compositions comprising enzymes, biocides or other medicament agents. In one specific embodiment the article of manufacture comprises clothing which shields the wearer from harmful environmental substances, for example, UV light, bacteria, viruses, air-borne toxins, gases, agents of chemical and/or biological warfare, workplace related chemical hazards and the like.

Coatings are typically converted to solid films after application to a substrate. For purposes of the present invention, "curing" is a process of film formation comprising forming a three-dimensional cross-linked network that is substantially insoluble in solvent and exhibits little or no flow when subjected to pressure. Curing is understood in the art to be a complex process that may be affected by multiple factors, including but not limited to solvent evaporation, film thickness, temperature, solvent concentration, reaction rates of cross-linking components and the presence, deliberate or inadvertant, of other materials. One skilled in the art will readily recognize that cure conditions impact the rate of film formation. Cure conditions selected for formation of the films according to the present invention are dependent upon the volatility of the solvent and the film thickness, but, in general, useable films occur between 5° C. and 200° C., and require between 30 seconds and 300 minutes after application to the substrate. The film and its final property profile may continue to develop after formation of a usable film, including from about five hours through and until about two weeks after application to the substrate.

The present invention also provides processes for making the novel crosslinkable compositions. In one embodiment the method comprises the steps of: a) dissolving a saccharide-siloxane copolymer in a suitable solvent to form a solution; b) dissolving at least one crosslinking agent in a suitable solvent to form a solution; c) adding the solution from b) into the solution from a) and mixing until b) is dispersed in a); and wherein the saccharide-siloxane copolymer comprises a reaction product of a functionalized organosiloxane polymer and at least one polyhydroxy-functional saccharide such that the organosiloxane polymer is covalently linked via a linking group to the at least one polyhydroxy-functional saccharide. In another embodiment the method comprises the steps of: a) dissolving a saccharide-siloxane copolymer in a suitable solvent to form a solution; b) adding at least one crosslinking agent directly into the solution from a) and, c) mixing until the crosslinking agent is dispersed in the solution from a).

The method for making a crosslinkable composition may further comprise additional steps which may be implemented nonsequentially at any point in the synthetic process. For instance, i) one or more additives may optionally be added into the solution formed in a) and then mixed until dispersed; ii) one or more additives may optionally be added contemporaneously with the crosslinking agent; and iii) one or more additives may optionally be added into the solution from c) and mixed until dispersed. One of ordinary skill in the art will recognize that the time frame for adding any desired additive will be dependent on the nature of that particular additive and how it is contemplated to be bound into the final matrix. It also depends upon whether it is contemplated that the additive will stay maximally bound, or be bound initially with time-dependent and/or pressure-sensitive release desired. The one or more additives may be selected from the group including d) a catalyst; e) a filler; f) a pigment; g) a UV stabilizer; h) a thermal stabilizer; i) a rheology modifier; j) a thickener; k) an adhesion promoter; l) a biocide; m) a preservative; n) an enzyme; o) a peptide; p) a reactive siloxane; q) a pressure sensitive adhesive, or p) a surface-active agent.

Suitable crosslinking agents comprise those discussed prior and as with respect to the synthetic result, the crosslinkers suitable for the present methods must be chemically reactive with hydroxyl groups and must be able to react with at least two hydroxyl groups and may be selected from the following: boric acid, borate ester (e.g. tri-n-propyl borate, triisopropanolamine borate), alkyl boronic acid or ester (e.g. phenyl boronic acid), titanate, (e.g. titanium isopropoxide, diisopropoxytitanium bis(acetylacetonate)), zirconate, glyoxal, gluteraldehyde, epichlorohydrin, urea-formaldehyde, zirconium ammonium carbonate, salt of a multivalent ion, bifunctional epoxy or glycidyl compounds (e.g. 1,4 butanediol diglycidyl ether), di-(N-hydroxymethyl)urea, di-isocyanate (e.g. toluene diisocyante, hexamethylene diisocyanate), 2-chloro N,N di-ethylacetamide, sodium trimetaphosphate, phosphorous oxychloride, acrolein, N-methyl urea, dicarboxylic acid, bis-acid chloride, dialkyldichlorosilane (e.g. dimethyldichlorosilane), alkyltrichlorosilane (e.g. Methyltrichlorosilane), reactive siloxane resin, and combinations thereof. In a specific method embodiment the crosslinking agent comprises a dicarboxylic acid and the one or more additives comprises a catalyst. In a very specific embodiment the catalyst comprises an enzyme, and in a very specific embodiment the enzyme comprises a lipase enzyme. In an even more specific embodiment the lipase comprises an immobilized form of *Candida antarctica* lipase B (CALB) marketed as N435 and available from Novozymes (Denmark).

One embodiment of the invention provides a novel crosslinked polymeric network formed from the novel crosslinkable compositions. The crosslinked networks may exhibit varying hybrid property profiles based on the particular siloxane and saccharide selected. In one embodiment the crosslinked network is in the form of an emulsion and provides a thickening function. In another embodiment the crosslinked network is incorporated into formulations contemplated to impart personal care benefits.

A further embodiment provides a cured coating composition formed from the novel crosslinkable compositions. In one specific embodiment the coating composition is self-catalyzing and self-curing. In another specific embodiment the coating composition comprises a catalyst to catalyze the curing process. One of ordinary skill in the art will appreciate that curing may occur through many routes and is dependent upon the particular crosslinking agent selected and the desirability of single-step or multiple step curing.

The cured coating compositions comprising the novel crosslinkable compositions are suitable for a variety of applications. As discussed above, the coatings may exhibit a hybrid property profile that combines characteristics of silicone-based films and coatings with characteristics of an organic, saccharide-based matrix. This unique property profile is adaptable by manipulating the selection of the components of the saccharide-siloxane. In addition, the coating properties and function is adaptable to a variety of applications by manipulating via the selection of optional additives included in the crosslinkable composition. The cured coating compositions may be pre-formed and adhered post-cure to substrates, or cure may be effected after application of the coating composition to a substrate.

One embodiment provides an article of manufacture comprising the novel cured coating composition. In a specific embodiment the article of manufacture comprises a textile and in a more specific embodiment the textile comprises clothing. In a very specific embodiment the clothing comprises a cured coating composition that provides a protective function wherein the cured coating composition comprises a crosslinkable composition comprising an additive capable of de-toxifying an environmental contaminant. In a very specific embodiment the additive comprises an enzyme. It is contemplated that such clothing may provide a protective or defensive benefit to people potentially subject to contaminated work environments or subject to chemical or biological warfare conditions. One of ordinary skill in the art will appreciate that there are other articles which desirably function as protective barriers and may comprise the present cured coating compositions adapted to provide this function.

Another embodiment provides an article of manufacture comprising a novel crosslinkable composition which functions as a temporary wound-healing enhancer. A specific embodiment is direct to a liquid band-aid which cures upon application to the skin and which is removable after a suitable period of time.

The following examples are merely illustrative of several embodiments of the present invention and should not be construed as limiting the scope of the invention as defined by the claims.

EXAMPLES

For Purposes of the following examples, ingredients identified by a proprietary designation are equivalent to the following generic descriptions:

| | |
|---|---|
| DC 0.65 cst 200 fluid | hexamethyldisiloxane |
| Cab-O-Sil TS-530 | hexamethyldisilazane treated silica |
| DC 245 Fluid | dimethylcyclosiloxane |
| DC 407 Resin | hydroxyl functional silicone resin in solvents |
| DC 6-3444 Resin | vinyl functional silicone resin in solvent |
| DC 7-4600 PSA | condensation reaction products between silanol functional siloxane and silicone resin |
| DC 7-4107 | silicone elastomer membrane |
| DC 2-8211, 2-8175 | aminosiloxane e.g. (dimethyl(methyl-isobutylethylenediamine)siloxane |

$$(Me)_3SiO[Me_2SiO]_x[MeSiO]_ySi(Me)_3$$
$$|$$
$$CH_2CH(CH_3)CH_2NHCH_2CH_2NH_2$$

| | |
|---|---|
| A12, 21, 32 | aminosiloxane (dimethyl(methylaminopropyl)siloxane) |

$$H_2NCH_2CH_2CH_2SiO[Me_2SiO]_xSiCH_2CH_2CH_2NH_2$$

Example 1

Crosslinkable Saccharide-Siloxane Copolymers

This example provides several illustrative embodiments of crosslinkable saccharide-siloxane copolymers and the synthesis thereof. Table 1, column 1 lists amine-functional siloxane polymers which may be covalently bound to either of two saccharide molecules listed in column 2, gluconolactone (GL) or lactobionolactone (LBL), to yield polyhydroxy-functional saccharide-siloxanes suitable for crosslinking. Table 2 further characterizes the amine-functional siloxane components. Note that in Table 2, "DTheory" indicates the degree of polymerization as the number of $(Me_2SiO)$ units present in the polymer backbone, and "mpc F" refers to the "mole percent functionality" which is the mole percentage of the isobutylethylene diamine groups. Below the tables is a list a-l of the copolymers from Table 1 and methods for their synthesis. These copolymers comprise the inventive crosslinkable copolymers which are employed in the remainder of the exemplary inventive embodiments.

TABLE 1

Saccharide-Siloxane Copolymer Descriptions

| Siloxane | Saccharide | Functionality:Saccharide | Solvent |
|---|---|---|---|
| A12 | GL | 1:1 | water |
| A21 | GL | 1:1 | heptane, cyclics |
| A32 | GL | 1:1 | heptane, cyclics |
| 8175 | GL | 1:1 | heptane, cyclics |
| 8211 | GL | 1:1 | heptane, cyclics |
| 8175/A12 | GL | 1:1 | dispersion in heptane, cyclics |
| A12 | LBL | 1:1 | dispersion in water |
| A21 | LBL | 1:1 | heptane, cyclics |
| A32 | LBL | 1:1 | heptane, cyclics |
| 8175 | LBL | 1:1 | heptane, cyclics |
| 8211 | LBL | 1:1 | heptane, cyclics |
| 8175/A12 | LBL | 1:1 | |

TABLE 2

Aminofunctional Polymers Employed

| polymer | cst | mw | % NH2 | Dp theory | mpc F | functional group |
|---|---|---|---|---|---|---|
| DMS-A12 | 20-30 | 950 | 3.1 | 20 | | aminopropyl |
| DMS-A21 | 100-120 | 5000 | 0.65 | 66 | | aminopropyl |
| DMS-A32 | 2000 | 27000 | 0.085 | 363 | | aminopropyl |
| 2-8175 | 150-400 | 7792 | | 100 | 2.3 | isobutyl-ethylenediamine |
| 2-8211 | 1000 | 22932 | | 300 | 1.9 | isobutyl-ethylenediamine | a) GL-A12

DMS-A12 (Gelest Inc., Morrisville, Pa.), a 20-30 cst. telechelic polydimethylsiloxane endblocked with aminopropyl groups, is reacted with gluconolactone (GL)(Sigma-Aldrich, St. Louis, Mo.) at 1:1 amine:lactone stoichiometry in methanol at 50° C. Upon completion of the reaction, the methanol is removed with rotary evaporation. The resulting material is a solid.

b) GL-A21

DMS-A21 (Gelest Inc., Morrisville, Pa.), a 100-320 cst. telechelic polydimethylsiloxane endblocked with aminopropyl groups, is reacted with gluconolactone (GL) (Sigma-Aldrich, St. Louis, Mo.) at 1:1 amine:lactone stoichiometry in methanol at 50° C. Upon completion of the reaction, the methanol is removed with rotary evaporation. The resulting material is a wax-like solid.

c) GL-A32

DMS-A32 (Gelest Inc., Morrisville, Pa.), a 2000 cst. telechelic polydimethylsiloxane endblocked with aminopropyl groups, is reacted with gluconolactone (GL)(Sigma-Aldrich, St. Louis, Mo.) at 1:1 amine:lactone stoichiometry in methanol at 50° C. Upon completion of the reaction, the methanol is removed with rotary evaporation. The resulting material has a gum-like consistency.

d) GL-8175

DC® Q2-8175 Fluid (Dow Corning Corp., Midland, Mich.), a 150-400 cst. polydimethylsiloxane with pendant aminoethylaminoisobutyl groups (approximately 2.3 mole percent), is reacted with gluconolactone at 1:1 primary amine:lactone stoichiometry in methanol at 50° C. Upon completion of the reaction, the methanol is removed with rotary evaporation. The resulting material has a gum-like consistency.

e) GL-8211

DC® 2-8211 Polymer (Dow Corning Corp. Midland, Mich.), a 1000 cst. polydimethylsiloxane with pendant aminoethylaminoisobutyl groups (approximately 1.9 mole percent), is reacted with gluconolactone at 1:1 primary amine:lactone stoichiometry in methanol at 50° C. Upon completion of the reaction, the methanol is removed with rotary evaporation. The resulting material has a gum-like consistency.

f) GL-8175/A12

DC® Q2-8175 Fluid (Dow Corning Corp., Midland, Mich.), a 150-400 cst. polydimethylsiloxane with pendant aminoethylaminoisobutyl groups (approximately 2.3 mole percent), and DMS-A12 are mixed together in a 1:1 by weight solution. This mixture is reacted with GL at a 1:1 primary amine:lactone stoichiometry in methanol at 50° C. Upon completion of the reaction, the methanol is removed with rotary evaporation. The resulting material has is a wax-like substance.

g) LBL-A12

DMS-A12 (Gelest Inc., Morrisville, Pa.), a 20-30 cst. telechelic polydimethylsiloxane endblocked with aminopropyl groups, is reacted with lactobionolactone (LBL)(prepared from lactobionic acid, Sigma-Aldrich, St. Louis, Mo.) at 1:1 amine:lactone stoichiometry in methanol at 50° C. Upon completion of the reaction, the methanol is removed with rotary evaporation. The resulting material is a solid.

h) LBL-A21

DMS-A21 (Gelest Inc., Morrisville, Pa.), a 100-320 cst. telechelic polydimethylsiloxane endblocked with aminopropyl groups, is reacted with lactobiolactone (LBL)(prepared from lactobionic acid, Sigma-Aldrich, St. Louis, Mo.) at 1:1 amine:lactone stoichiometry in methanol at 50° C. Upon completion of the reaction, the methanol is removed with rotary evaporation. The resulting material is wax-like.

i) LBL-A32

DMS-A32 (Gelest Inc., Morrisville, Pa.), a 2000 cst. telechelic polydimethylsiloxane endblocked with aminopropyl groups, is reacted with lactobiolactone (LBL)(prepared from lactobionic acid, Sigma-Aldrich, St. Louis, Mo.) at 1:1 amine:lactone stoichiometry in methanol at 50° C. Upon completion of the reaction, the methanol is removed with rotary evaporation. The resulting material is wax-like.

j) LBL-8175

DC® Q2-8175 Fluid (Dow Corning Corp., Midland, Mich.), a 150-400 cst. polydimethylsiloxane with pendant aminoethylaminoisobutyl groups (approximately 2.3 mole percent), is reacted with lactobionolactone (LBL) (prepared from lactobionic acid, Sigma-Aldrich, St. Louis Mo.) at 1:1 primary amine:lactone stoichiometry in methanol at 50° C. Upon completion of the reaction, the methanol is removed with rotary evaporation. The resulting material is wax-like.

k) LBL-8211

DC® 2-8211 Polymer (Dow Corning Corp., Midland, Mich.), a 1000 cst. polydimethylsiloxane with pendant aminoethylaminoisobutyl groups (approximately 1.9 mole percent), is reacted with lactobionolactone (LBL) (prepared from lactobionic acid, Sigma-Aldrich, St. Louis Mo.) at 1:1 primary amine:lactone stoichiometry in methanol at 50° C. Upon completion of the reaction, the methanol is removed with rotary evaporation. The resulting material is a rubbery powder.

l) LBL-8175/A12

DC® Q2-8175 Fluid (Dow Corning Corp., Midland, Mich.), a 150-400 cst. polydimethylsiloxane with pendant aminoethylaminoisobutyl groups (approximately 2.3 mole percent), and DMS-A12 (Gelest Inc., Morrisville, Pa.), a 20-30 cst. telechelic polydimethylsiloxane endblocked with aminopropyl groups are mixed together in a 1:1 by weight solution. This mixture is reacted with LBL at 1:1 primary amine:lactone stoichiomethry in methanol at 50° C. Upon completion of the reaction, the methanol is removed with rotary evaporation. The resulting material is wax-like.

Test Protocols Employed Herein:

1. Swell-Gel for determination of crosslinking. For purposes of characterizing the compositions illustrated in the following examples, determination of crosslinking is conducted by the following "swell-gel" method. A sample of a crosslinked film is placed in a large volume of a compatible solvent. Over time, the film swells to accommodate the solvent. After a specified amount of time the solvent swollen film is poured over an 80 mesh stainless steel screen. Excess solvent is quickly blotted and a solvent swollen weight is obtained. Percent swell is reported as solvent swollen weight divided by initial film weight multiplied by 100. The remaining solvent is then evaporated and the dry sample weight is recorded. Any unreacted polymer will have been extracted into the solvent, so the remaining weight represents the reacted polymer. This is reported as percent gel. It is calculated by dividing the dry weight by the initial weight and multiplied by 100. Specifically as employed herein, 0.01-0.2 g of a film is weighed out and placed into a 2 ounce bottle. 40 g of heptane are added to the bottle and gently agitated until the film is suspended in the solvent. After two hours the swollen film and solvent are poured over an 80 mesh stainless steel screen to capture the swollen film. Excess solvent is quickly blotted and a weight obtained. The solvent is evaporated at room temperature overnight and the film is then re-weighted. Percent swell and percent gel are reported.

2. Smear/Rub-off/Migration Testing for Cure Characteristics of Paper coatings. The cure characteristics of paper coating materials under specified curing conditions are evaluated using laboratory scale coating techniques which are designed to match actual production coating conditions. The cure of the film is evaluated in three manners: 1) Smearing under finger pressure, 2) Rub-off under finger pressure, and 3) Migration or transfer of the cured coating to adhesive tape. The observations are given numerical ratings with the higher values indicating more complete cure. The procedure may be used to determine a suitable cure cycle by varying cure conditions until a fully cured coating is obtained which yields no smear, no rub-off and no migration.

In this procedure, one clean dry piece of the specified substrate is selected. The coating bath formulation is prepared and the substrate is coated as specified. The substrate is transferred to the oven rack and secured in place. The rack is placed in an oven that has been conditioned and stabilized at a specified temperature. After a specified time, the substrate is removed from the oven and allowed to cool to room temperature at normal room conditions (about 10 min). The substrate is placed on a hard flat surface. The following observations are made:

a) Smear: make a single track by drawing a finger tip, using hard pressure, over a length of about 10 cm. Observe the greasy marking, and report as the appropriate numerical rating:
  5=None
  4=Very slight
  3=Slight
  2=Some
  1=Gross b) Rub-off: make a new single track by drawing a finger tip, using hard pressure, over a length of about 10 cm five times in the same direction. Rub-off is felt as a balling of the film or as particles of film on the substrate or as a gummy tacky feeling. Report as the appropriate numerical rating:
  4=None
  3=Very slight
  2=Slight
  1=Gross c) Migration: apply a fresh 15 cm long piece of the specified adhesive tape (adhesive side down) to the coated substrate with a light finger pressure. Allow it to remain in contact for about 30 s. Remove the tape in a single smooth pull. If it does not strip freely, report "Fail", report a rating or repeat the coating and cure. Without using any more pressure than necessary to make them stick together, double the tape, adhesive side in, to form a loop about 3 cm in diameter with the surfaces touching. Slowly pull the ends apart and observe the loop. Report the appropriate numerical rating:
  3=None (the adhesive/adhesive interface moves along the tape as the loop is pulled apart, i.e., the loop becomes smaller.)
  2=Slight (the loop begins to reduce in size before the tape pulls apart.)
  1=Gross (the tape pulls apart immediately with no reduction in the size of the loop.

3. Film-Formation techniques. With respect to film formation, films of saccharide siloxanes can be formed using any of the standard film draw down techniques including, draw down bars, wire-wound rods, and shims. Films may also be formed by simply pouring the solution onto release coatings like polyethylene, or into glass or plastic sample dishes. A person of ordinary skill in the art will appreciate the many methods known in the art suitable for forming the films described herein, and that any method employed in a particular example disclose herein may be substituted for by other equally suitable methods.

4. Skim Milk Plate Protocol in test for protease presence. 15 mm mylar disks which have the test formulation on them are cut out and pressed into the skim milk/agar. The disk becomes less opaque as it makes contact with the plate. A negative control disk containing either an enzyme-free formulation or mylar alone is also pressed into the plate. The plate or petri dish is closed and allowed to sit at either 25 or 37° C. A small clearing circle (where the agar/skim milk turns from turbid to transparent) appears directly under the test disk and slowly expands in a concentric circle around the test disk. The recipe for making skim milk/agar plates is:

Formula:

| Formula: | |
|---|---|
| Skim Milk-Difco | 5 g |
| dH2O to | 50 ml |
| In a separate bottle: | |
| Yeast Extract-Difco | 2.5 g |
| NaCl | 0.5 g |
| Bacto Agar | 10 g |
| dH2O to | 450 ml |

Autoclave the solutions separately. Allow to cool to 50° C. Combine (add the skim to the agar). Add 1 ml of 10 mg/ml Chloramphenicol.

5. Swellometer (OSB Testing) Test Protocol. The following steps are followed:
  1. Cut, identify and weigh (within 5 minutes of removal from the humidity chamber) wood wafer samples and record the identification number and weight in logbook;
  2. Fill a pan with the blended emulsion or solution to be tested.
    a. Immediately wet one side of the wood and then quickly flip the board to immediately wet the other side. Failure to do so will bow the wood and it will only partially soak.
    b. Allow the wood to soak on both sides for 90 seconds (3 minutes total for water based solutions)
    c. Soak for 30 seconds for solvent based solutions (15 seconds for each side)
    d. Remove the wood from the soak bath and dry for 1 minute, and weigh. (record the data)
  3. Place the wood wafers on a drying rack for 24 hours and try to get them to rest at a 45 degree angle for drying.
  4. Place the wood wafers after the 24 hour drying time back into the humidity chamber for 6 days then repeat the top listed step on the $6^{th}$ and $7^{th}$ day.
  5. Place a full bucket of deionized water on the bench top early in the morning on the $7^{th}$ day of testing. This will allow the temperature of the water to reach room temperature which is required for testing.
6. Place the stop pin in the bottom of the dial indicating swellometer device. Slide the test sample into slotted area firmly against the stop pin.
7. Adjust the dial gauge up or down and tighten close to the 0.0 dial indicating position. Fine tuning of the zero point can be completed by adjusting the outer edge of the dial. Do this step prior to placing the sample into the water bath for testing.
8. Place the apparatus with the sample into the water bath for 30 minutes. Adjust the bath height by adding water if needed, so that the entire sample in submerged in the water.
9. Record the dial reading for each sample.
10. Remove from the water
11. Dry/clean test apparatus
12. Remove the sample from the test jig and towel dry, and record the final wet weight.
13. Complete the computer data sheet information, and then enter final results into logbook.
14. Report the calculated results.

Example 2

Formation of a Crosslinked Network

This example illustrates confirmation that a crosslinked network forms in a solution comprising the GL-8211 copolymer and a suitable crosslinker, in contrast to the absence of a crosslinked network in the same solution without a crosslinker.

a) 44.13 g of the GL-8211 copolymer and 396.88 g of heptane are mixed until the copolymer dissolves. 2.5 g of this solution is placed on a foil weigh pan and placed in an oven at 70 C for 15 minutes to evaporate the solvent. The resulting film is not elastomeric and has a slight tack.

b) 10 g of the copolymer/heptane solution is weighed into a disposable plastic cup. 1 g of a 2% solution of tri-n-propyl borate in heptane is added to the cup and mixed using a Hauschild Speedmixer (Flacktek Inc) for 20 seconds. The solution becomes a gel. 1.66 g of the solution is placed on an aluminum weigh dish and placed in a 70 C oven for 35 minutes. An elastomeric film remains.

Example 3

High-Release Coating on a Paper Substrate

This example illustrates that a composition comprising a saccharide-siloxane copolymer and a crosslinking agent forms a high-release coating on Kraft paper whereas the same composition without a crosslinking agent fails to form a coating on Kraft paper.

a) 150.09 g of the copolymer/heptane solution from example 2a is further mixed with 165 g of heptane until dispersed. This solution is coated onto 53# Rhinelander SCK Kraft paper using a #14 Meyer rod. The solvent is removed by passing the coated substrate thru a 300 F oven for 23.5 seconds. The evaluation for Smear, Rub-off and Migration was moderate-gross (numerically defined as "1") for all three subtests. This is numerically defined as 1/1/1.

b) 150 g of the copolymer/heptane solution prepared in Example 2a is further mixed with 150 g of heptane and 15 g a 2% solution of tri-n-propyl borate in heptane until dispersed. This solution is coated onto 53# Rhinelander SCK Kraft paper using a #14 Meyer rod. The solvent is removed by passing the coated substrate thru a 300 F oven for 23.5 seconds. The evaluation for Smear, Rub-off, and Migration is slight (numerical equivalent=1) smear, moderate-gross (numerical equivalent=2) rub-off, and slight (numerical equivalent=1) migration, showing improvement in integrity over the film formed in 3a.

c) The coated Kraft paper from b) is tested for release using both a rubber based adhesive tape and an acrylic based adhesive tape according to FINAT Test Method No. 3 and No. 4 (FTM 3 and FTM 4). The results are reported in Table 3:

TABLE 3

| sample # | in/min | Acrylic grams-force | Rubber grams-force |
|---|---|---|---|
| 130A | 12 | 527 | 168 |
|  | 40 | 672 | 193 |

Theses results indicate that the saccharide-siloxane film has utility as a release coating for paper especially where high release is desired.

Example 4

Confirmation of Film-Forming

The following example illustrates that in the absence of a crosslinker, most of the saccharide-siloxane copolymer dissolves in the heptane, while in the presence of a borate crosslinking agent, the copolymer is not soluble in heptane because it is bound into a three-dimensional network and remains in the film.

A solution of the copolymer GL-8211 comprising, by weight, 50% saccharide siloxane, 6.4% ethanol and 43.6% DC 0.65 cst 200 fluid is prepared. A film of this material is cast on a polyethylene sheet and becomes tack-free after solvent evaporation at room temperature. Swell-gel analysis is performed using heptane. The percent gel is 27.6 indicating that most of the film sample had dissolved in the heptane. This result is commensurate with most of the copolymer being unbound. A second film is prepared from an 8.1% solution of GL-8211 in DC 0.65 cst 200 Fluid containing 1.1 parts of $B(OPr)_3$ per 100 pts GL-8211. After solvent evaporation at room temperature a clear, tack free film remains. Swell-gel analysis is again performed using heptane. The percent swell is 650 and the percent gel is 89, indicating the formation of a crosslinked network.

Example 5

Film Comprising a Bound Enzyme

This example illustrates an embodiment providing a film formed from a crosslinked network of saccharide-siloxanes wherein the three-dimensional network of the film comprises a bound enzyme, Protease B.

A film is prepared from an 8.3% solution of GL-8211 in DC 0.65 cst 200 Fluid containing 1.1 parts of $B(OPr)_3$ per 100 pts GL-8211 and 3.5 parts of a 42 mg/ml protease enzyme solution per 100 pts GL-8211. After solvent evaporation at room temperature a clear, tack free film remains. Swell-gel analysis is performed using heptane. The percent swell is 593 and the percent gel is 75, indicating the formation of a crosslinked network.

Example 6

Crosslinkable Composition Further Comprising a Filler

This example illustrates that a film formed from a crosslinkable composition comprising saccharide-siloxane copolymer, a borate ester crosslinker and a silica filler exhibits tighter networking.

A film is prepared from an 8.0% solution of copolymer GL-8211 in DC 0.65 cst 200 Fluid containing 1.0 parts of $B(OPr)_3$ per 100 parts GL-8211 and 19.8 parts Cab-O-Sil TS-530 fumed silica per 100 parts GL-8211. After solvent evaporation at room temperature a hazy, tack free film remains. Swell-gel analysis is performed using heptane. The percent swell is 347 and the percent gel is 89, indicating the formation of a crosslinked network.

Example 7

Crosslinked Network Formed in Different Solvent

The following example illustrates that a crosslinkable composition comprising a saccharide-siloxane copolymer and a borate ester crosslinker will still crosslink when delivered from a different solvent. It further illustrates that the crosslinker concentration can be lowered.

A film is prepared from a solution comprising 6.3% GL-8211, 92% DC 245 Fluid, 0.8% ethanol, 0.8% DC 0.65 cst 200 Fluid and 0.1% $B(OPr)_3$. After solvent evaporation at room temperature a clear, tack free film remains. Swell-gel analysis is performed using heptane. The percent swell is 543 and the percent gel is 79, indicating the formation of a crosslinked network.

Example 8

Crosslinking Agent Comprises a Reactive Siloxane Resin

The following example illustrates that a crosslinkable composition comprising a saccharide-siloxane copolymer and a hydroxyl functional reactive siloxane resin crosslinker forms an insoluble film indicating the reactive resin is an effective crosslinker at a 25 pts resin to 100 pts saccharide-siloxane.

A film is prepared from a solution comprising 42.5% GL-8211, 10.6% DC 407 resin, 5.4% ethanol, 37.0% DC 0.65 cst 200 Fluid, and 4.5% xylene. After solvent evaporation at room temperature a clear, tack free film remains. Swell-gel analysis is performed using heptane. The percent swell is 260 and the percent gel is 94, indicating the formation of a crosslinked network.

Example 9

Crosslinking Agent Comprises a Reactive Siloxane Resin

The following example illustrates that a crosslinkable composition comprising a saccharide-siloxane copolymer and a hydroxyl functional reactive siloxane resin crosslinker forms an insoluble film indicating the reactive resin is an effective crosslinker at a 28 pts resin to 100 pts saccharide-siloxane.

A film is prepared from a solution comprising 34% GL-8211, 9.6% DC 407 resin, 4.3% ethanol, 29.6% DC 0.65 cst 200 Fluid, and 22.5% DC 245 Fluid. After solvent evaporation at room temperature a clear, tack free film remains. Swell-gel analysis is performed using heptane. The percent swell is 219 and the percent gel is 92, indicating the formation of a crosslinked network.

Example 10

Crosslinking Agent Comprises Vinyl-Functional Reactive Siloxane

The following example illustrates that a crosslinkable composition comprising a saccharide-siloxane copolymer and a vinyl functional reactive siloxane resin crosslinker forms an insoluble film, indicating the reactive resin is an effective crosslinker at 40 pts resin to 100 pts saccharide-siloxane.

A film is prepared from a solution comprising 38.3% GL-8211, 15.2% DC 6-3444 resin, 3.6% ethanol, 34% DC 0.65 cst 200 Fluid, and 8.9% xylene. After solvent evaporation at room temperature a clear, tack free film remains. Swell-gel analysis is performed using heptane. The percent swell is 289 and the percent gel is 88, indicating the formation of a crosslinked network.

Example 11

Crosslinked Network Comprising Protease B

The following example illustrates that a crosslinkable composition comprising a saccharide-siloxane copolymer, borate ester crosslinking agent, and an enzyme forms a crosslinked film upon solvent evaporation and, subsequently, the film slowly releases the enzyme and the free enzyme maintains its bioactivity. Incorporating the hydrophilic saccharide moiety onto the backbone of an organosiloxane and then crosslinking the copolymers provides a unique matrix which is compatible with the hydrophilic enzyme.

10.29 g of 6.65% GL-8211 in hexamethyldisiloxane and 0.69 g of 2% tripropylborate in hexamethyldisiloxane are mixed in a Hauschild AM-501 dental mixer. 5.001 g of this solution is then diluted with 2.014 g of 13.5% GL-8211. Subsequently 0.021 g of Protease B enzyme is added to the mixture. After each addition step, the sample is mixed two times in a Hauschild AM-501 dental mixer. The prepared solution is poured into a petri dish in order to dry and cure it into a thin film over 24 hours. From the cured, dried film, samples are cut out and analyzed for enzyme release activity. The enzyme release is followed on a skim milk plate.

Figure 1B:
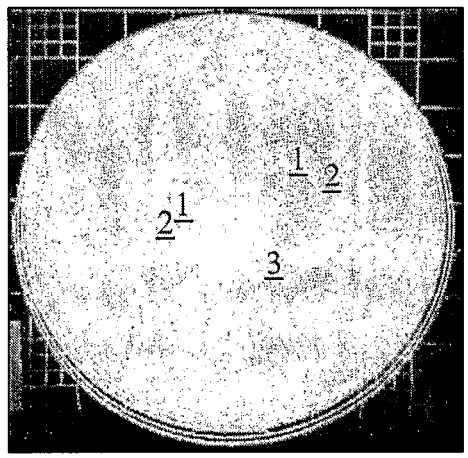

The skim milk plate is prepared as follows: in one bottle, skim milk powder is dissolved in water, and, in an other bottle, yeast extract sodium chloride and agar are mixed together. The bottles are autoclaved at 121° C. for 15 minutes using a Hirayama Autoclave. They are then cooled to 45° C. in a water bath. Afterward, the skim milk solution is added to the agar and the combined solution is poured into petri dishes and allowed to solidify. A small piece of the saccharide-siloxane matrix containing the enzyme is cut out and pressed into the skim milk agar. The petri dish plate is allowed to incubate at 30±2° C. FIG. 1 shows that enzyme is released from the prepared patch on a skim milk plate observed after 24 hours incubation.

Example 12

Slow Release of Protease B Enzyme from Crosslinked Matrix

This experiment illustrates the slow release of Protease B enzyme from a film formed from a Crosslinkable composition comprising saccharide siloxane, a crosslinking agent and a pressure sensitive adhesive network matrix further comprising Protease B.

11.91 g of 14.61% GL-8211 in hexamethyldisiloxane, 0.41 g of Glycerin and 0.42 g of Protease B enzyme from a 42 mg/ml stock solution are mixed in a Hauschild AM-501 dental mixer. 8.04 g of 75% DC7-4600 Pressure Sensitive Adhesive in hexamethyldisiloxane is added to this mixture. After each addition step, the sample is mixed two times in a Hauschild AM-501 dental mixer. The prepared emulsion is spread on DC7-4107 silicone membrane/Polycarbonate substrate using a draw down bar made by Paul N. Gardner Company, Inc. The drawn film is allowed to dry to a thin film on the substrate over 24 hours in a ventilated hood. From the dried film, patches are cut out and analyzed for enzyme release activity. The enzyme release is followed on a skim milk plate.

Figure 2A:
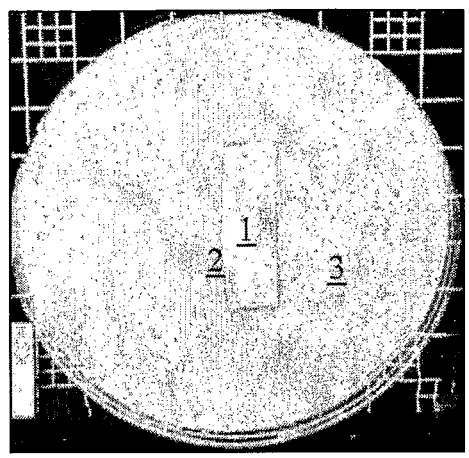
FIG. 2: illustrates the release of a small amount of Protease B enzyme from a prepared saccharide-siloxane copolymer/PSA formulation patch on a skim milk plate after 24 hours incubation.
Figure 2B:
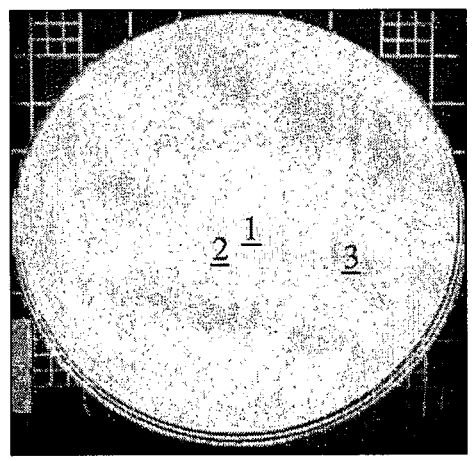

The skim milk plate is prepared as follows: in one bottle, skim milk powder is dissolved in water, and, in an other bottle, yeast extract sodium chloride and agar are mixed together. The bottles are autoclaved at 121° C. for 15 minutes using a Hirayama Autoclave. They are cooled to 45° C. in a water bath. Afterward, the skim milk solution is added to the agar and the combined solution is poured into petri dishes and allowed to solidify. A small piece of the silicone carbohydrate matrix containing the enzyme is cut out and pressed into the skim milk agar. The petri dish plate is allowed to incubate at 30±2° C. FIG. 2 shows that small amount of enzyme is released from the prepared patch on a skim milk plate observed after 24 hours incubation.

Example 13

Healthcare Films

The following example illustrates that reinforced crosslinked saccharide-siloxane films can be prepared which have substantivity to skin and lower friction of the skin surface. Non-limiting examples of the utility of this embodiment include application as liquid wound dressings or liquid bandages.

45 g of GL-8211 saccharide-siloxane are diluted with a 90/10 by weight solution of 0.65 cst. 200 Fluid (Dow Corning Corp, Midland Mich.) and 200 proof ethanol until a 50% copolymer concentration is achieved. The dilution is accomplished by sequential additions of the solvent followed by mixing on a Hauschild Speedmixer™ centrifugal mixer (Flacktek, Inc. Landrum, S.C.) until homogenous.

Crosslinker A is a 10% by weight solution of triisopropanolamine borate (Anderson Development Co., Adrian, Mich.) in 200 proof ethanol. Croslinker B is a 10% by weight solution of phenyl boronic acid (Sigma-Aldrich Co., St. Louis, Mo.) in 200 proof ethanol. Cab-o-sil TS-530 is a hexamethyldisilazane treated silica (Cabot Co. Boston, Mass.)

The saccharide-siloxane solution, treated silica, and crosslinker solutions are by mixed on a Hauschild Speedmixer™ centrifugal mixer (Flacktek, Inc. Landrum, S.C.) until homogenous. 10 mil films are drawn and allowed to dry. A small sample is swabbed on the knuckles of either hand and allowed to dry into a film.

Table 4 shows the compositions and results achieved.

These results illustrate that the surface feel of the films can be improved by the additions of treated silica and that using a difunctional borate can extend the pot life. The substantivity is also demonstrated. These features are important for a liquid applied wound dressing.

The invention claimed is:

1. A cross-linkable composition comprising:
a) a saccharide-siloxane copolymer;
b) a crosslinking agent; and
c) optionally, solvent,
wherein the saccharide-siloxane copolymer has the following formula:

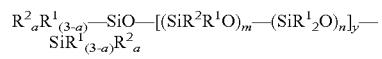

wherein each $R^1$ can be the same or different and comprises hydrogen, $C_1$-$C_{12}$ alkyl, an organic radical, or $R^3$-Q, Q comprises an epoxy, cycloepoxy, primary or secondary amino, ethylenediamine, carboxy, halogen, vinyl, allyl, anhydride, or mercapto functionality, m and n are integers from 0 to 10,000 and may be the same or different, each a is independently 0, 1, 2, or 3, provided that if a is 0 then m is from 1 to 10,000 and if m is 0, then a is 1, 2 or 3, y is an integer such that the copolymer has a molecular weight less than 1 million, $R^2$ has the formula Z-$(G^1)_b$-$(G^2)_c$, and there is at least one $R^2$ per copolymer, wherein $G^1$ is a saccharide component comprising 5 to 12 carbons, b+c is 1-10, b or c can be 0, $G^2$ is a saccharide component comprising 5 to 12 carbons additionally substituted with organic or organosilicon radicals, Z is the linking group and is independently selected from the group consisting of:
—$R^3$—NHC(O)—$R^4$—;
—$R^3$—NHC(O)O—$R^4$—;
—$R^3$—NH—C(O)—NH—$R^4$—;
—$R^3$—C(O)—O—$R^4$—;
—$R^3$—O—$R^4$—;
—$R^3$—CH(OH)—$CH_2$—O—$R^4$—;
—$R^3$—S—$R^4$
—$R^3$—CH(OH)—$CH_2$—NH—$R^4$—; and
—$R^3$—N($R^1$)—$R^4$, and $R^3$ and $R^4$ are divalent spacer groups comprising $(R^5)_r(R^6)_s(R^7)_t$, wherein at least one of r, s and t must be 1, and $R^5$ and $R^7$ are independently an alkylene group of 1 to 12 carbons or a group of formula $(R^9O)_p$ wherein p is any integer 1-50, each $R^9$ is a divalent organic group of 1 to 12 carbons and each $R^9O$ may be the same or different, $R^6$ is —N($R^8$)—, where $R^8$ is H or $C_1$-$C_{12}$ alkyl, and at least one of $R^3$ and $R^4$ must be present in the linking group and may be the same or different, wherein the saccharide-siloxane copolymer comprises a reaction product of a functionalized organosiloxane polymer and at least one polyhydroxy-functional sac-

TABLE 4

| Saccharide-siloxane solution (grams) | Crosslinker A (grams) | Crosslinker B (grams) | Cab-o-sil TS-530 (grams) | Friction | Substantivity (hours) | pot life (hours) |
|---|---|---|---|---|---|---|
| 5 | 0.5 | — | — | obvious drag | — | <24 |
| 5 | 0.5 | — | 0.45 | much smoother | 24-72 | <24 |
| 5 | — | 0.5 | 0.45 | much smoother | 24-72 | >24 | charide such that the organosiloxane is covalently linked via the linking group, Z, to the at least one polyhydroxy-functional saccharide.

2. The cross-linkable composition of claim 1 wherein the saccharide-siloxane copolymer comprises a hydroxyl functionality of at least three.

3. The cross-linkable composition of claim 1 wherein the linking group comprises an amide, an amino, a urethane, a urea, an ester, an ether, a thioether, or an acetal linking group.

4. The cross-linkable composition of claim 1 further including a catalyst.

5. The cross-linkable composition of claim 1, wherein the catalyst comprises an enzyme capable catalyzing an esterification or a transesterification reaction.

6. The cross-linkable composition of claim 1 further including a biocide.

7. The cross-linkable composition of claim 1 further including a preservative.

8. The cross-linkable composition of claim 1 further including a peptide.

9. The cross-linkable composition of claim 1 further including a surface-active agent.

10. The cross-linkable composition of claim 1 further including an enzyme.

11. The cross-linkable composition of claim 10, wherein the enzyme comprises a lipase.

12. The cross-linkable composition of claim 10, wherein the enzyme comprises Protease B.

13. The cross-linkable composition of claim 10, wherein the crosslinking agent is boric acid, borate ester, alkyl or aryl boronic acid or ester, and combinations thereof.

14. The cross-linkable composition of claim 10 further including the solvent, the solvent comprising at least one nonpolar organic solvent.

15. The cross-linkable composition of claim 10 further including the solvent, the solvent comprising a volatile silicone/nonpolar organic solvent and alcohol.

16. An article comprising a textile, the textile including a cross-linkable composition, the cross-linkable composition comprising:
a) a saccharide-siloxane copolymer;
b) a crosslinking agent; and
c) optionally, solvent,
wherein the saccharide-siloxane copolymer has the following formula:

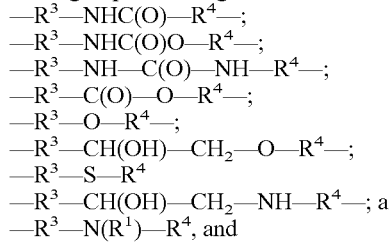

wherein each $R^1$ can be the same or different and comprises hydrogen, $C_1$-$C_{12}$ alkyl, an organic radical, or $R^3$-Q,
Q comprises an epoxy, cycloepoxy, primary or secondary amino, ethylenediamine, carboxy, halogen, vinyl, allyl, anhydride, or mercapto functionality,
m and n are integers from 0 to 10,000 and may be the same or different, each a is independently 0, 1, 2, or 3, provided that if a is 0 then m is from 1 to 10,000 and if m is 0, then a is 1, 2 or 3,
y is an integer such that the copolymer has a molecular weight less than 1 million,
$R^2$ has the formula Z-$(G^1)_b$-$(G^2)_c$, and there is at least one $R^2$ per copolymer, wherein $G^1$ is a saccharide component comprising 5 to 12 carbons, b+c is 1-10, b or c can be 0,
$G^2$ is a saccharide component comprising 5 to 12 carbons additionally substituted with organic or organosilicon radicals, Z is the linking group and is independently selected from the group consisting of:
—$R^3$—NHC(O)—$R^4$—;
—$R^3$—NHC(O)O—$R^4$—;
—$R^3$—NH—C(O)—NH—$R^4$—;
—$R^3$—C(O)—O—$R^4$—;
—$R^3$—O—$R^4$—;
—$R^3$—CH(OH)—$CH_2$—O—$R^4$—;
—$R^3$—S—$R^4$
—$R^3$—CH(OH)—$CH_2$—NH—$R^4$—; and
—$R^3$—N($R^1$)—$R^4$, and
$R^3$ and $R^4$ are divalent spacer groups comprising $(R^5)_r$-$(R^6)_s$-$(R^7)_t$, wherein at least one of r, s and t must be 1, and
$R^5$ and $R^7$ are independently an alkylene group of 1 to 12 carbons or a group of formula $(R^9O)_p$ wherein p is any integer 1-50, each $R^9$ is a divalent organic group of 1 to 12 carbons and each $R^9O$ may be the same or different,
$R^6$ is —N($R^8$)—, where $R^8$ is H or $C_1$-$C_{12}$ alkyl,
and at least one of $R^3$ and $R^4$ must be present in the linking group and may be the same or different,
wherein the saccharide-siloxane copolymer comprises a reaction product of a functionalized organosiloxane polymer and at least one polyhydroxy-functional saccharide such that the organosiloxane is covalently linked via the linking group, Z, to the at least one polyhydroxy-functional saccharide.

17. The article of claim 16, wherein the textile is an item of clothing.

18. The cross-linkable composition of claim 1 wherein the linking group comprises an amide, an amino, a urethane or a urea.

19. A cross-linkable composition comprising:
a) a saccharide-siloxane copolymer;
b) a crosslinking agent; and
c) optionally, solvent,
wherein the saccharide-siloxane copolymer has the following formula:

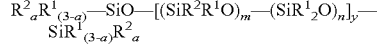

wherein each $R^1$ can be the same or different and comprises hydrogen, $C_1$-$C_{12}$ alkyl, an organic radical, or $R^3$-Q,
Q comprises an epoxy, cycloepoxy, primary or secondary amino, ethylenediamine, carboxy, halogen, vinyl, allyl, anhydride, or mercapto functionality,
m and n are integers between 0 and 10,000 and may be the same or different, a is independently 0, 1, 2, or 3, provided that if a is 0 then mi is from 1 to 10,000 and if m is 0, then a is 1, 2 or 3,
y is an integer such that the copolymer has a molecular weight less than 1 million,
$R^2$ has the formula Z-$(G^1)_b$-$(G^2)_c$, and there is at least one $R^2$ per copolymer, wherein $G^1$ is a saccharide component comprising 5 to 12 carbons, b+c is 1-10, b or c can be 0, either b or c must be 1,
$G^2$ is a saccharide component comprising 5 to 12 carbons additionally substituted with organic or organosilicon radicals,
Z is the linking group and is independently selected from the group consisting of:
—$R^3$—NHC(O)—$R^4$—;
—$R^3$—NHC(O)O—$R^4$—;
—$R^3$—NH—C(O)—NH—$R^4$—;
—$R^3$—C(O)—O—$R^4$—;
—$R^3$—O—$R^4$—;
—$R^3$—S—$R^4$
—$R^3$—CH(OH)—$CH_2$—O—$R^4$—

—$R^3$—CH(OH)—$CH_2$—NH—$R^4$—; and
—$R^3$—N($R^1$)—$R^4$, and $R^3$ and $R^4$ are divalent spacer groups comprising $(R^5)_r(R^6)_s(R^7)_t$, where at least one of r, s and t must be 1, and $R^5$ and $R^7$ are independently an alkylene group of 1 to 12 carbons or a group of formula $(R^9O)_p$ wherein p is any integer 1-50, each $R^9$ is a divalent organic group of 1 to 12 carbons and each $R^9O$ may be the same or different, $R^6$ is —N($R^8$)—, where $R^8$ is H or $C_1$-$C_{12}$ alkyl, and at least one of $R^3$ and $R^4$ must be present in the linking group and may be the same or different, and wherein the crosslinking agent is selected from the group consisting of boric acid, borate ester, alkyl or aryl boronic acid or ester, titanate, zirconate, glyoxal, gluteraldehyde, epichlorohydrin, urea-formaldehyde, zirconium ammonium carbonate, salt of a multivalent ion, 1,4 butanediol diglycidyl ether, di-(N-hydroxymethyl)urea, di-isocyanate, 2-chloro N,N di-ethylacteamide, sodium trimetaphosphate, phosphorous oxychloride, acrolein, N-methyl urea, dicarboxylic acid, bis-acid chloride, dialkyldichlorosilane, alkyltricholorosilane, reactive siloxane resin and combinations thereof, wherein the saccharide-siloxane copolymer comprises a reaction product of a functionalized organosiloxane polymer and at least one polyhydroxy-functional saccharide such that the organosiloxane is covalently linked via the linking group, Z, to the at least one polyhydroxy-functional saccharide.

20. The cross-linkable composition of claim 19 wherein the linking group comprises an amide, an amino, a urethane or a urea.

21. An article comprising a textile, the textile including a cross-linkable composition, the cross-linkable composition comprising:
a) a saccharide-siloxane copolymer;
b) a crosslinking agent; and
c) optionally, solvent,
wherein the saccharide-siloxane copolymer has the following formula:

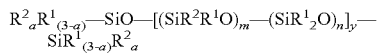
$R^2_a R^1_{(3-a)}$—SiO—$[(SiR^2R^1O)_m$—$(SiR^1_2O)_n]_y$—$SiR^1_{(3-a)}R^2_a$ wherein each $R^1$ can be the same or different and comprises hydrogen, $C_1$-$C_{12}$ alkyl, an organic radical, or $R^3$-Q, Q comprises an epoxy, cycloepoxy, primary or secondary amino, ethylenediamine, carboxy, halogen, vinyl, allyl, anhydride, or mercapto functionality, m and n are integers from 0 to 10,000 and may be the same or different, a is independently 0, 1, 2, or 3, y is an integer such that the copolymer has a molecular weight less than 1 million, $R^2$ has the formula Z-$(G^1)_b$-$(G^2)_c$, and there is at least one $R^2$ per copolymer, wherein $G^1$ is a saccharide component comprising 5 to 12 carbons, b+c is 1-10, b or c can be 0, $G^2$ is a saccharide component comprising 5 to 12 carbons additionally substituted with organic or organosilicon radicals, Z is the linking group and is independently selected from the group consisting of:
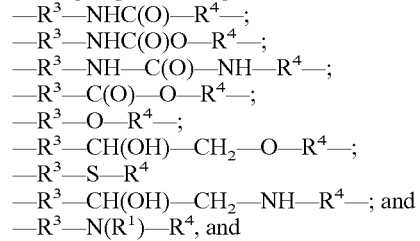
—$R^3$—NHC(O)—$R^4$—;
—$R^3$—NHC(O)O—$R^4$—;
—$R^3$—NH—C(O)—NH—$R^4$—;
—$R^3$—C(O)—O—$R^4$—;
—$R^3$—O—$R^4$—;
—$R^3$—CH(OH)—$CH_2$—O—$R^4$—;
—$R^3$—S—$R^4$
—$R^3$—CH(OH)—$CH_2$—NH—$R^4$—; and
—$R^3$—N($R^1$)—$R^4$, and $R^3$ and $R^4$ are divalent spacer groups comprising $(R^5)_r(R^6)_s(R^7)_t$, wherein at least one of r, s and t must be 1, and $R^5$ and $R^7$ are independently an alkylene group of 1 to 12 carbons or a group of formula $(R^9O)_p$ wherein p is any integer 1-50, each $R^9$ is a divalent organic group of 1 to 12 carbons and each $R^9O$ may be the same or different, $R^6$ is —N($R^8$)—, where $R^8$ is H or $C_1$-$C_{12}$ alkyl, and at least one of $R^3$ and $R^4$ must be present in the linking group and may be the same or different, wherein the crosslinking agent is selected from the group consisting of boric acid, borate ester, alkyl or aryl boronic acid or ester, titanate, zirconate, glyoxal, gluteraldehyde, epichlorohydrin, urea-formaldehyde, zirconium ammonium carbonate, salt of a multivalent ion, 1,4 butanediol diglycidyl ether, di-(N-hydroxymethyl)urea, di-isocyanate, 2-chloro N,N di-ethylacteamide, sodium trimetaphosphate, phosphorous oxychloride, acrolein, N-methyl urea, dicarboxylic acid, bis-acid chloride, dialkyldichlorosilane, alkyltricholorosilane, reactive siloxane resin and combinations thereof, wherein the saccharide-siloxane copolymer comprises a reaction product of a functionalized organosiloxane polymer and at least one polyhydroxy-functional saccharide such that the organosiloxane is covalently linked via the linking group, Z, to the at least one polyhydroxy-functional saccharide.

22. The article of claim 21, wherein the textile is an item of clothing.

* * * * *